United States Patent
Soltani et al.

(10) Patent No.: US 10,888,657 B2
(45) Date of Patent: Jan. 12, 2021

(54) METHOD AND APPARATUS FOR TREATMENT OF INTRACRANIAL HEMORRHAGES

(75) Inventors: Azita Soltani, Snohomish, WA (US); Raymond M. Wolniewcz, III, Redmond, WA (US); Brenton Nistal, Seattle, WA (US); Curtis Genstler, Snohomish, WA (US); Robert L. Wilcox, Bothell, WA (US); Ronald L. Haas, Kirkland, WA (US)

(73) Assignee: EKOS CORPORATION, Bothell, WA (US)

( * ) Notice: Subject to any disclaimer, the term of this patent is extended or adjusted under 35 U.S.C. 154(b) by 449 days.

(21) Appl. No.: 13/219,403

(22) Filed: Aug. 26, 2011

(65) Prior Publication Data

US 2012/0059285 A1    Mar. 8, 2012

Related U.S. Application Data

(60) Provisional application No. 61/377,639, filed on Aug. 27, 2010.

(51) Int. Cl.
| | |
|---|---|
| *A61B 17/22* | (2006.01) |
| *A61B 18/00* | (2006.01) |
| *A61B 90/00* | (2016.01) |
| *A61M 5/158* | (2006.01) |
| *A61H 1/00* | (2006.01) |

(52) U.S. Cl.
CPC ......... *A61M 5/158* (2013.01); *A61B 17/2202* (2013.01); *A61B 90/39* (2016.02); *A61B 2017/22021* (2013.01); *A61B 2017/22028* (2013.01); *A61B 2017/22084* (2013.01); *A61B 2018/00821* (2013.01); *A61B 2217/005* (2013.01); *A61M 2205/058* (2013.01);
(Continued)

(58) Field of Classification Search
CPC .............................. A61N 7/00; A61H 23/0245
USPC ............................................................. 601/2
See application file for complete search history.

(56) References Cited

U.S. PATENT DOCUMENTS

| | | |
|---|---|---|
| 3,352,303 A | 11/1967 | Delaney |
| 3,430,625 A | 3/1969 | McLeod, Jr. |

(Continued)

FOREIGN PATENT DOCUMENTS

| | | |
|---|---|---|
| CA | 1083040 | 8/1980 |
| CN | 1193267 A | 9/1998 |

(Continued)

OTHER PUBLICATIONS

International Search Report and Written Opinion dated Apr. 23, 2012, in International Application No. PCT/US2011/049456 in 11 pages.

(Continued)

*Primary Examiner* — Hien N Nguyen
(74) *Attorney, Agent, or Firm* — Seager, Tufte & Wickhem, LLP

(57) ABSTRACT

An ultrasound catheter with a lumen for fluid delivery and fluid evacuation, and an ultrasound source is used for the treatment of intracerebral or intraventricular hemorrhages. After the catheter is inserted into a blood clot, a lytic drug can be delivered to the blood clot via the lumen while applying ultrasonic energy to the treatment site. As the blood clot is dissolved, the liquefied blood clot can be removed by evacuation through the lumen.

22 Claims, 16 Drawing Sheets

(52) U.S. Cl.
CPC .............. *A61M 2205/3368* (2013.01); *A61M 2210/0693* (2013.01)

(56) References Cited

U.S. PATENT DOCUMENTS

| | | |
|---|---|---|
| 3,565,062 A | 2/1971 | Kuris |
| 3,827,115 A | 8/1974 | Bom |
| 3,861,391 A | 1/1975 | Antonevich et al. |
| 3,941,122 A | 3/1976 | Jones |
| 4,192,294 A | 3/1980 | Gekhman et al. |
| 4,309,989 A | 1/1982 | Fahim |
| 4,319,580 A | 3/1982 | Colley |
| 4,354,502 A | 10/1982 | Colley et al. |
| 4,682,596 A | 7/1987 | Bales et al. |
| 4,692,139 A | 9/1987 | Stiles |
| 4,808,153 A | 2/1989 | Parisi |
| 4,870,953 A | 10/1989 | Donmicheal |
| 4,936,281 A | 6/1990 | Stasz |
| 4,953,565 A | 9/1990 | Tachibana et al. |
| 4,971,991 A | 11/1990 | Umemura et al. |
| 5,058,570 A | 10/1991 | Idemoto et al. |
| 5,069,664 A | 12/1991 | Guess |
| 5,076,276 A | 12/1991 | Sakurai et al. |
| 5,088,499 A | 2/1992 | Unger |
| 5,163,421 A | 11/1992 | Bernstein |
| 5,163,436 A | 11/1992 | Saitoh et al. |
| 5,197,946 A | 3/1993 | Tachibana |
| 5,261,291 A | 11/1993 | Schoch et al. |
| 5,267,954 A | 12/1993 | Nita |
| 5,269,291 A | 12/1993 | Carter |
| 5,279,546 A | 1/1994 | Mische et al. |
| 5,304,115 A | 4/1994 | Pflueger |
| 5,307,816 A | 5/1994 | Hashimoto |
| 5,315,998 A | 5/1994 | Tachibana et al. |
| 5,318,014 A | 6/1994 | Carter |
| 5,326,342 A | 7/1994 | Pflueger |
| 5,342,292 A | 8/1994 | Nita et al. |
| 5,344,395 A | 9/1994 | Whalen et al. |
| 5,345,940 A | 9/1994 | Seward |
| 5,362,309 A | 11/1994 | Carter |
| 5,368,557 A | 11/1994 | Nita |
| 5,368,558 A | 11/1994 | Nita |
| 5,380,273 A | 1/1995 | Dubrul et al. |
| 5,401,237 A | 3/1995 | Tachibana et al. |
| 5,423,797 A | 6/1995 | Adrian et al. |
| 5,431,663 A | 7/1995 | Carter |
| 5,440,914 A | 8/1995 | Tachibana et al. |
| 5,447,509 A | 9/1995 | Mills et al. |
| 5,454,782 A | 10/1995 | Perkins |
| 5,456,259 A | 10/1995 | Barlow et al. |
| 5,474,530 A | 12/1995 | Passafaro |
| 5,474,531 A | 12/1995 | Carter |
| 5,498,236 A | 3/1996 | Dubrul et al. |
| 5,509,896 A | 4/1996 | Carter |
| 5,542,917 A | 8/1996 | Nita et al. |
| 5,542,935 A | 8/1996 | Unger et al. |
| 5,558,092 A | 9/1996 | Unger et al. |
| 5,582,586 A | 12/1996 | Tachibana et al. |
| 5,603,327 A | 2/1997 | Eberle |
| 5,606,974 A | 3/1997 | Castellano |
| 5,620,409 A | 4/1997 | Gans et al. |
| 5,624,382 A | 4/1997 | Oppelt |
| 5,630,837 A | 5/1997 | Crowley |
| 5,648,098 A | 7/1997 | Porter |
| 5,660,909 A | 8/1997 | Tachibana et al. |
| 5,681,296 A | 10/1997 | Ishida |
| 5,695,460 A | 12/1997 | Siegel et al. |
| 5,720,710 A | 2/1998 | Tachibana et al. |
| 5,724,976 A | 3/1998 | Hirama et al. |
| 5,725,494 A | 3/1998 | Brisken |
| 5,728,062 A | 3/1998 | Brisken |
| 5,752,930 A | 5/1998 | Baudino et al. |
| 5,772,627 A | 6/1998 | Acosta et al. |
| 5,823,962 A | 10/1998 | Lerch et al. |
| 5,824,005 A | 10/1998 | Motamedi et al. |
| 5,827,203 A | 10/1998 | Nita |
| 5,834,880 A | 11/1998 | Lewandowski et al. |
| 5,840,031 A | 11/1998 | Crowley |
| 5,846,218 A | 12/1998 | Brisken et al. |
| 5,876,345 A | 3/1999 | Eaton et al. |
| 5,925,016 A | 7/1999 | Chornenky et al. |
| 5,928,186 A | 7/1999 | Homsma et al. |
| 5,934,284 A | 8/1999 | Plaia et al. |
| 5,957,851 A | 9/1999 | Hossack |
| 5,957,882 A | 9/1999 | Nita et al. |
| 5,971,949 A | 10/1999 | Levin et al. |
| 5,976,120 A | 11/1999 | Chow et al. |
| 5,997,497 A | 12/1999 | Nita et al. |
| 6,001,069 A | 12/1999 | Tachibana et al. |
| 6,024,718 A | 2/2000 | Chen et al. |
| 6,044,845 A | 4/2000 | Lewis et al. |
| 6,063,069 A | 5/2000 | Cragg et al. |
| 6,066,123 A | 5/2000 | Bednarski et al. |
| 6,088,613 A | 7/2000 | Unger |
| 6,089,573 A | 7/2000 | Udagawa |
| 6,096,000 A | 8/2000 | Tachibana et al. |
| 6,113,570 A | 9/2000 | Siegel et al. |
| 6,117,101 A | 9/2000 | Diederich et al. |
| 6,135,976 A | 10/2000 | Tachibana et al. |
| 6,144,869 A | 11/2000 | Berner et al. |
| 6,149,596 A | 11/2000 | Bancroft |
| 6,176,842 B1 | 1/2001 | Tachibana et al. |
| 6,206,831 B1 | 3/2001 | Suorsa et al. |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,235,024 B1 | 5/2001 | Tu |
| 6,238,347 B1 | 5/2001 | Nix et al. |
| 6,270,460 B1 | 8/2001 | McCartan et al. |
| 6,277,077 B1 | 8/2001 | Brisken et al. |
| 6,287,271 B1 | 9/2001 | Dubrul et al. |
| 6,295,990 B1 | 10/2001 | Lewis et al. |
| 6,296,619 B1 | 10/2001 | Brisken et al. |
| 6,312,402 B1 | 11/2001 | Hansmann |
| 6,322,513 B1 | 11/2001 | Schregel |
| 6,356,776 B1 | 3/2002 | Berner et al. |
| 6,361,554 B1 | 3/2002 | Brisken |
| 6,391,042 B1 | 5/2002 | Cimino |
| 6,394,956 B1 | 5/2002 | Chandrasekaran et al. |
| 6,398,772 B1 | 6/2002 | Bond et al. |
| 6,398,792 B1 | 6/2002 | O'Connor |
| 6,416,740 B1 | 7/2002 | Unger |
| 6,435,189 B1 | 8/2002 | Lewis et al. |
| 6,454,737 B1 | 9/2002 | Nita et al. |
| 6,454,757 B1 | 9/2002 | Nita et al. |
| 6,464,680 B1 | 10/2002 | Brisken et al. |
| 6,471,683 B2 | 10/2002 | Drasier et al. |
| 6,478,765 B2 | 11/2002 | Siegel et al. |
| 6,482,309 B1 * | 11/2002 | Green .................. A61L 2/035 204/242 |
| 6,494,891 B1 | 12/2002 | Cornish et al. |
| 6,506,584 B1 | 1/2003 | Chandler et al. |
| 6,524,251 B2 | 2/2003 | Rabiner et al. |
| 6,524,271 B2 | 2/2003 | Brisken et al. |
| 6,551,337 B1 | 4/2003 | Rabiner et al. |
| 6,558,366 B1 | 5/2003 | Drasler et al. |
| 6,562,021 B1 | 5/2003 | Derbin et al. |
| 6,565,552 B1 | 5/2003 | Barbut |
| 6,575,956 B1 | 6/2003 | Brisken et al. |
| 6,579,277 B1 | 6/2003 | Rabiner et al. |
| 6,582,392 B1 | 6/2003 | Bennett et al. |
| 6,585,678 B1 | 7/2003 | Tachibana et al. |
| 6,589,253 B1 | 7/2003 | Cornish et al. |
| 6,594,514 B2 | 7/2003 | Berner et al. |
| 6,605,084 B2 | 8/2003 | Acker et al. |
| 6,623,444 B2 | 9/2003 | Babaev |
| 6,635,046 B1 | 10/2003 | Barbut |
| 6,645,150 B2 | 11/2003 | Angelsen et al. |
| 6,647,755 B2 | 11/2003 | Rabiner et al. |
| 6,652,547 B2 | 11/2003 | Rabiner et al. |
| 6,660,013 B2 | 12/2003 | Rabiner |
| 6,663,613 B1 | 12/2003 | Evans et al. |
| 6,676,626 B1 | 1/2004 | Bennett et al. |

(56) References Cited

U.S. PATENT DOCUMENTS

| | | |
|---|---|---|
| 6,682,502 B2 | 1/2004 | Bond et al. |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,785 B2 | 2/2004 | Brisken et al. |
| 6,699,269 B2 | 3/2004 | Khanna |
| 6,723,063 B1 | 4/2004 | Zhang et al. |
| 6,723,064 B2 | 4/2004 | Babaev |
| 6,726,698 B2 | 4/2004 | Cimino |
| 6,730,048 B1 | 5/2004 | Hare et al. |
| 6,733,451 B2 | 5/2004 | Rabiner et al. |
| 6,733,515 B1 | 5/2004 | Edwards et al. |
| 6,740,040 B1 | 5/2004 | Mandrusov et al. |
| 6,767,345 B2 | 7/2004 | St. Germain et al. |
| 6,796,992 B2 | 9/2004 | Barbut |
| 6,824,575 B1 | 11/2004 | Otomo et al. |
| 6,830,577 B2 | 12/2004 | Nash et al. |
| 6,849,062 B2 | 2/2005 | Kantor |
| 6,850,790 B2 | 2/2005 | Berner et al. |
| 6,855,123 B2 | 2/2005 | Nita |
| 6,866,670 B2 | 3/2005 | Rabiner et al. |
| 6,905,505 B2 | 6/2005 | Dodson, Jr. et al. |
| 6,921,371 B2 | 7/2005 | Wilson |
| 6,929,632 B2 | 8/2005 | Nita et al. |
| 6,929,633 B2 | 8/2005 | Evans et al. |
| 6,942,620 B2 | 9/2005 | Nita et al. |
| 6,942,677 B2 | 9/2005 | Nita et al. |
| 6,945,937 B2 | 9/2005 | Culp et al. |
| 6,958,040 B2 | 10/2005 | Oliver |
| 6,979,293 B2 | 12/2005 | Hansmann et al. |
| 6,985,771 B2 | 1/2006 | Fischell et al. |
| 7,025,425 B2 | 4/2006 | Kovalchev et al. |
| 7,084,118 B2 | 8/2006 | Armstrong et al. |
| 7,137,963 B2 | 11/2006 | Nita et al. |
| 7,141,044 B2 | 11/2006 | Gentsler |
| 7,166,098 B1 | 1/2007 | Steward et al. |
| 7,174,199 B2 | 2/2007 | Berner et al. |
| 7,186,246 B2 | 3/2007 | Bennett et al. |
| 7,220,233 B2 | 5/2007 | Nita et al. |
| 7,220,239 B2 | 5/2007 | Wilson et al. |
| 7,300,414 B1 | 11/2007 | Holland et al. |
| 7,308,303 B2 | 12/2007 | Whitehurst et al. |
| 7,309,334 B2 | 12/2007 | von Hoffmann |
| 7,335,180 B2 | 2/2008 | Nita et al. |
| 7,341,569 B2 | 3/2008 | Soltani et al. |
| 7,384,407 B2 | 6/2008 | Rodriguez et al. |
| 7,503,895 B2 | 3/2009 | Rabiner et al. |
| 7,540,852 B2 | 6/2009 | Nita et al. |
| 7,567,016 B2 | 7/2009 | Lu et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,648,478 B2 | 1/2010 | Soltani et al. |
| 7,717,853 B2 | 5/2010 | Nita |
| 7,727,178 B2 | 6/2010 | Wilson |
| 7,758,509 B2 | 7/2010 | Angelsen et al. |
| 7,771,372 B2 | 8/2010 | Wilson |
| 7,774,933 B2 | 8/2010 | Wilson et al. |
| 7,789,830 B2 | 9/2010 | Fujita et al. |
| 7,818,854 B2 | 10/2010 | Wilson |
| 7,828,754 B2 | 11/2010 | Abe et al. |
| 7,828,762 B2 | 11/2010 | Wilson |
| 7,874,985 B2 | 1/2011 | Kovatchev et al. |
| 7,901,359 B2 | 3/2011 | Mandrusov et al. |
| 7,914,509 B2 | 3/2011 | Bennett et al. |
| 8,012,092 B2 | 9/2011 | Powers et al. |
| 8,062,566 B2 | 11/2011 | Nita et al. |
| 8,123,789 B2 | 2/2012 | Khanna |
| 8,152,753 B2 | 4/2012 | Nita et al. |
| 8,167,831 B2 | 5/2012 | Wilson |
| 8,192,363 B2 | 6/2012 | Soltani et al. |
| 8,192,391 B2 | 6/2012 | Soltani |
| 8,366,620 B2 | 2/2013 | Nita |
| 8,696,612 B2 | 4/2014 | Wilson et al. |
| 8,740,835 B2 | 6/2014 | Soltani et al. |
| 9,044,568 B2 | 6/2015 | Wilcox et al. |
| 9,107,590 B2 | 8/2015 | Hansmann et al. |
| 9,192,566 B2 | 11/2015 | Soltani et al. |
| 9,579,494 B2 | 2/2017 | Kersten et al. |
| 10,182,833 B2 | 1/2019 | Soltani et al. |
| 10,188,410 B2 | 1/2019 | Soltani et al. |
| 2002/0032394 A1 | 3/2002 | Brisken et al. |
| 2002/0052620 A1 | 5/2002 | Barbut |
| 2002/0045890 A1 | 6/2002 | Celliers et al. |
| 2002/0082238 A1 | 6/2002 | Newman et al. |
| 2002/0068869 A1 | 8/2002 | Brisken et al. |
| 2002/0123787 A1 | 9/2002 | Weiss |
| 2002/0133081 A1* | 9/2002 | Ackerman et al. ........... 600/486 |
| 2002/0133111 A1 | 9/2002 | Shadduck |
| 2002/0077550 A1 | 10/2002 | Rabiner et al. |
| 2002/0193708 A1 | 12/2002 | Thompson et al. |
| 2002/0198526 A1* | 12/2002 | Shaolian ............ A61B 17/1671 606/254 |
| 2003/0013986 A1 | 1/2003 | Saadat |
| 2003/0036705 A1 | 2/2003 | Hare et al. |
| 2003/0040501 A1 | 2/2003 | Newman et al. |
| 2003/0050662 A1 | 3/2003 | Don Michael |
| 2003/0065263 A1 | 4/2003 | Hare et al. |
| 2003/0069525 A1 | 4/2003 | Brisken et al. |
| 2003/0083608 A1 | 5/2003 | Evans et al. |
| 2003/0083698 A1 | 5/2003 | Whitehurst et al. |
| 2003/0088187 A1* | 5/2003 | Saadat .................. A61B 5/015 600/547 |
| 2003/0163147 A1 | 8/2003 | Hare et al. |
| 2003/0187320 A1 | 10/2003 | Freyman |
| 2003/0199831 A1* | 10/2003 | Morris et al. ................. 604/174 |
| 2003/0220568 A1 | 11/2003 | Hansmann et al. |
| 2003/0236539 A1 | 12/2003 | Rabiner et al. |
| 2004/0001809 A1 | 1/2004 | Brisken et al. |
| 2004/0024347 A1 | 2/2004 | Wilson et al. |
| 2004/0039311 A1 | 2/2004 | Nita et al. |
| 2004/0019318 A1 | 3/2004 | Wilson et al. |
| 2004/0049148 A1 | 3/2004 | Rodriguez et al. |
| 2004/0059313 A1 | 3/2004 | Anderson et al. |
| 2004/0068189 A1* | 4/2004 | Wilson et al. ................ 600/459 |
| 2004/0097996 A1 | 5/2004 | Hare et al. |
| 2004/0122354 A1 | 6/2004 | Semba |
| 2004/0138570 A1 | 7/2004 | Nita et al. |
| 2004/0162571 A1 | 8/2004 | Rabiner et al. |
| 2004/0171981 A1 | 9/2004 | Buffen et al. |
| 2004/0220514 A1 | 11/2004 | Cafferata |
| 2004/0236350 A1 | 11/2004 | Bolduc et al. |
| 2004/0255957 A1 | 12/2004 | Cafferata |
| 2004/0265393 A1 | 12/2004 | Unger et al. |
| 2005/0021063 A1 | 1/2005 | Hall et al. |
| 2005/0043753 A1 | 2/2005 | Rabiner et al. |
| 2005/0043629 A1 | 5/2005 | Rabiner et al. |
| 2005/0124877 A1 | 6/2005 | Nita et al. |
| 2005/0137520 A1 | 6/2005 | Rule et al. |
| 2005/0177212 A1 | 8/2005 | Njemanze |
| 2005/0187513 A1 | 8/2005 | Rabiner et al. |
| 2005/0187514 A1 | 8/2005 | Rabiner et al. |
| 2005/0197619 A1 | 9/2005 | Rule et al. |
| 2005/0209578 A1 | 9/2005 | Evans et al. |
| 2005/0215942 A1* | 9/2005 | Abrahamson et al. ......... 604/22 |
| 2005/0215946 A1 | 9/2005 | Hansmann et al. |
| 2005/0216044 A1 | 9/2005 | Hong |
| 2005/0096669 A1 | 10/2005 | Rabiner et al. |
| 2005/0256410 A1 | 11/2005 | Rabiner et al. |
| 2005/0113688 A1 | 12/2005 | Nita et al. |
| 2005/0119679 A1 | 12/2005 | Rabiner et al. |
| 2006/0069303 A1 | 3/2006 | Couvillon |
| 2006/0078555 A1 | 4/2006 | Hanley et al. |
| 2006/0094947 A1 | 5/2006 | Kovalchev et al. |
| 2006/0106308 A1 | 5/2006 | Hansmann et al. |
| 2006/0106375 A1* | 5/2006 | Werneth et al. ................ 606/32 |
| 2006/0142524 A1 | 6/2006 | Lewis et al. |
| 2006/0173387 A1 | 8/2006 | Hansmann et al. |
| 2006/0184070 A1 | 8/2006 | Hansmann et al. |
| 2006/0241462 A1 | 10/2006 | Chou et al. |
| 2006/0264758 A1* | 11/2006 | Hossack et al. ............... 600/467 |
| 2007/0005121 A1* | 1/2007 | Khanna ........................ 607/104 |
| 2007/0016040 A1 | 1/2007 | Nita |
| 2007/0016041 A1 | 1/2007 | Nita |

(56) References Cited

U.S. PATENT DOCUMENTS

| | | |
|---|---|---|
| 2007/0037119 A1 | 2/2007 | Pal et al. |
| 2007/0038100 A1 | 2/2007 | Nita |
| 2007/0038158 A1 | 2/2007 | Nita et al. |
| 2007/0066978 A1 | 3/2007 | Schafer et al. |
| 2007/0083100 A1 | 4/2007 | Schulz-Stubner |
| 2007/0112296 A1* | 5/2007 | Wilson et al. .......... 604/22 |
| 2007/0123652 A1 | 5/2007 | Chu et al. |
| 2007/0129652 A1 | 6/2007 | Nita |
| 2007/0142721 A1 | 6/2007 | Berner et al. |
| 2007/0225619 A1 | 9/2007 | Rabiner et al. |
| 2007/0239027 A1 | 10/2007 | Nita |
| 2007/0265560 A1 | 11/2007 | Soltani et al. |
| 2008/0045865 A1 | 2/2008 | Kislev |
| 2008/0065014 A1 | 3/2008 | McCrystle et al. |
| 2008/0146918 A1 | 6/2008 | Magnin et al. |
| 2008/0154181 A1 | 6/2008 | Khanna |
| 2008/0167602 A1 | 7/2008 | Nita et al. |
| 2008/0171965 A1 | 7/2008 | Soltani et al. |
| 2008/0172067 A1 | 7/2008 | Nita et al. |
| 2008/0194954 A1 | 8/2008 | Matsunaga et al. |
| 2008/0221506 A1 | 9/2008 | Rodriguez et al. |
| 2008/0262350 A1 | 9/2008 | Abrahamson et al. |
| 2008/0249501 A1 | 10/2008 | Yamasaki |
| 2008/0306499 A1 | 12/2008 | Katoh et al. |
| 2008/0312536 A1* | 12/2008 | Dala-Krishna .......... 600/459 |
| 2008/0319355 A1 | 12/2008 | Nita |
| 2008/0319376 A1 | 12/2008 | Wilcox et al. |
| 2009/0018472 A1 | 1/2009 | Soltani et al. |
| 2009/0099482 A1 | 4/2009 | Furuhata et al. |
| 2009/0112150 A1 | 4/2009 | Unger et al. |
| 2009/0209900 A1 | 8/2009 | Carmeli et al. |
| 2009/0216246 A1 | 8/2009 | Nita et al. |
| 2010/0010393 A1 | 1/2010 | Duffy et al. |
| 2010/0022920 A1 | 1/2010 | Nita et al. |
| 2010/0022944 A1 | 1/2010 | Wilcox |
| 2010/0023036 A1 | 1/2010 | Nita et al. |
| 2010/0023037 A1 | 1/2010 | Nita et al. |
| 2010/0049209 A1 | 2/2010 | Nita et al. |
| 2010/0063413 A1 | 3/2010 | Volz |
| 2010/0063414 A1 | 3/2010 | Volz |
| 2010/0081934 A1 | 4/2010 | Hansmann et al. |
| 2010/0125193 A1 | 5/2010 | Zadicario |
| 2010/0143325 A1 | 6/2010 | Gurewich |
| 2010/0160779 A1 | 6/2010 | Browning et al. |
| 2010/0160780 A1 | 6/2010 | Swan et al. |
| 2010/0196348 A1 | 8/2010 | Armstrong et al. |
| 2010/0204582 A1 | 8/2010 | Lu |
| 2010/0210940 A1 | 8/2010 | Bradley et al. |
| 2010/0217276 A1 | 8/2010 | Garrison et al. |
| 2010/0222715 A1 | 9/2010 | Nita |
| 2010/0256616 A1 | 10/2010 | Katoh et al. |
| 2010/0262215 A1 | 10/2010 | Gertner |
| 2010/0292685 A1 | 11/2010 | Katoh et al. |
| 2010/0317952 A1 | 12/2010 | Budiman et al. |
| 2010/0331645 A1 | 12/2010 | Simpson et al. |
| 2010/0332142 A1 | 12/2010 | Shadforth et al. |
| 2011/0009720 A1 | 1/2011 | Kunjan et al. |
| 2011/0009739 A1 | 1/2011 | Phillips et al. |
| 2011/0034791 A1 | 2/2011 | Moerman |
| 2011/0160621 A1 | 6/2011 | Nita |
| 2011/0200578 A1 | 8/2011 | Hanley et al. |
| 2011/0288449 A1 | 11/2011 | Schenkengel |
| 2011/0313328 A1 | 12/2011 | Nita |
| 2011/0319927 A1 | 12/2011 | Nita |
| 2012/0016272 A1 | 1/2012 | Nita et al. |
| 2012/0041307 A1 | 2/2012 | Patel et al. |
| 2012/0078140 A1 | 3/2012 | Nita |
| 2012/0123273 A1 | 5/2012 | Okuno et al. |
| 2012/0179073 A1 | 7/2012 | Nita |
| 2012/0197277 A1 | 8/2012 | Stinis |
| 2012/0209116 A1 | 8/2012 | Hossack et al. |
| 2012/0265123 A1 | 10/2012 | Khanna |
| 2012/0271223 A1 | 10/2012 | Khanna |
| 2012/0330196 A1 | 12/2012 | Nita |
| 2013/0211316 A1 | 8/2013 | Wilcox et al. |
| 2014/0276367 A1 | 9/2014 | Kersten et al. |
| 2016/0030725 A1 | 2/2016 | Kersten et al. |
| 2017/0182302 A1 | 6/2017 | Kersten et al. |

FOREIGN PATENT DOCUMENTS

| | | |
|---|---|---|
| CN | 1309331 A | 8/2001 |
| EP | 0 617 913 | 10/1994 |
| EP | 0744189 | 11/1996 |
| EP | 1090658 | 4/2001 |
| EP | 1 145 731 | 10/2001 |
| EP | 2 494 932 | 9/2012 |
| JP | 06-233779 | 8/1994 |
| JP | 08-243168 | 9/1996 |
| JP | 2001-228601 | 8/2001 |
| JP | 2002-501402 | 1/2002 |
| JP | 2002-519095 | 7/2002 |
| JP | 2003-509152 | 3/2003 |
| JP | 2005-512630 | 5/2005 |
| JP | 2006-055649 | 3/2006 |
| JP | 2006-510449 | 3/2006 |
| JP | 2007-520281 | 7/2007 |
| JP | 2009-508630 | 3/2009 |
| WO | WO 94/017734 | 8/1994 |
| WO | WO 96/27341 | 9/1996 |
| WO | WO 96/29935 | 10/1996 |
| WO | WO 96/36286 | 11/1996 |
| WO | WO 98/040016 | 9/1998 |
| WO | WO 98/048711 | 11/1998 |
| WO | WO 99/033500 | 7/1999 |
| WO | WO 99/33550 | 7/1999 |
| WO | WO 99/39647 | 8/1999 |
| WO | WO 00/000095 | 1/2000 |
| WO | WO 00/012004 | 3/2000 |
| WO | WO 00/38580 | 7/2000 |
| WO | WO 02/13678 | 2/2002 |
| WO | WO 02/15803 | 2/2002 |
| WO | WO 02/15804 | 2/2002 |
| WO | WO 03/051208 | 6/2003 |
| WO | WO 2004/058045 | 7/2004 |
| WO | WO 05/027756 | 3/2005 |
| WO | WO 05/084552 | 9/2005 |
| WO | WO 05/084553 | 9/2005 |
| WO | WO 2008/052186 | 5/2008 |
| WO | WO 2009/002881 | 12/2008 |
| WO | WO 2012/027722 | 3/2012 |
| WO | WO 2014/159274 | 10/2014 |

OTHER PUBLICATIONS

Non-final Office Action dated Dec. 4, 2012 in U.S. Appl. No. 12/008,611.

Chamsuddin et al., "Catheter-directed Thrombolysis with the Endowave System in the Treatment of Acute Massive Pulmonary Embolism: A Retrospective Multicenter Case Series," Journal of Vascular and Interventional Radiology, Mar. 2008, vol. 19, No. 3, pp. 372-376.

International Preliminary Report on Patentability in Application No. PCT/US2011/049456, dated Mar. 14, 2013.

Lin et al., "Comparison of Percutaneous Ultrasound-Accelerated Thrombolysis versus Catheter-Directed Thrombolysis in Patients with Acute Massive Pulmonary Embolism," Vascular, 2009, vol. 17, No. 3, pp. S137-S147.

Akdemir et al., "Treatment of Severe Intraventricular Hemorrhage by Intraventricular Infusion of Urokinase", Neurosurgical Review, 1995, vol. 18, No. 2, pp. 95-100.

Broderick et al., "Guidelines for the Management of Spontaneous Intracerebral Hemorrhage: A Statement for Healthcare Professionals From a Special Writing Group of the Stroke Council, American Heart Association", Stroke, Journal of the American Heart Association, 1999, pp. 905-915.

Deinsberger et al., "Stereotactic Aspiration and Fibrinolysis of Spontaneous Supratentorial Intracerebral Hematomas versus Conservative Treatment: A Matched-Pair Study", Zentralblatt für Neurochirurgie, Dec. 18, 2003, vol. 64, No. 4, pp. 145-150.

(56) References Cited

OTHER PUBLICATIONS

Findlay et al., "Lysis of Intraventricular Hematoma with Tissue Plasminogen Activator", Journal of Neurosurgery, 1991, vol. 74, pp. 803-807.

Matsumoto et al., "CT-Guided Stereotaxic Evacuation of Hypertensive Intracerebral Hematomas", Journal of Neurosurgery, Sep. 1984, vol. 61, No. 3, pp. 440-448.

Mayfrank et al., "Fibrinolytic Treatment of Intraventricular Haemorrhage Preceding Surgical Repair of Ruptured Aneurysms and Arteriovenous Malformations", British Journal of Neurosurgery, 1999, vol. 13, No. 2, pp. 128-131.

Mohadjer et al., "CT-Guided Stereotactic Fibrinolysis of Spontaneous and Hypertensive Cerebellar Hemorrhage: Long-Term Results", Journal of Neurosurgery, Aug. 1990, vol. 73, No. 2, pp. 217-222.

Niizuma et al., "CT-Guided Stereotactic Aspiration of Intracerebral Hematoma—Result of a Hematoma-Lysis Method Using Urokinase", Applied Neurophysiology, Proceedings of the Ninth Meeting of the World Society, Jul. 4-7, 1985, pp. 4.

Niizuma et al., "Results of Stereotactic Aspiration in 175 Cases of Putaminal Hemorrhage", Neurosurgery, Jun. 1989, vol. 24, No. 6, pp. 814-819.

Official Communication in Japanese Patent Application No. 2013-526188, dated Jun. 9, 2015.

Pang et al., "Lysis of Intraventricular Blood Clot with Urokinase in a Canine Model: Part 1", Neurosurgery, 1986, vol. 19, No. 4, pp. 540-546.

Rohde et al., "Intraventricular Recombinant Tissue Plasminogen Activator for Lysis of Intraventricular Haemorrhage", Journal of Neurology and Neurosurgery Psychiatry, 1995, vol. 58, pp. 447-451.

Schaller et al., "Stereotactic Puncture and Lysis of Spontaneous Intracerebral Hemorrhage Using Recombinant Tissue-Plasminogen Activator", Neurosurgery, Feb. 1995, vol. 36, No. 2, pp. 328-335.

Teernstra et al., "Stereotactic Treatment of Intracerebral Hematoma by Means of a Plasminogen Activator. A Multicenter Randomized Controlled Trial (SICHPA", Stroke, Journal of the American Heart Association, Mar. 20, 2003, pp. 968-974.

\* cited by examiner

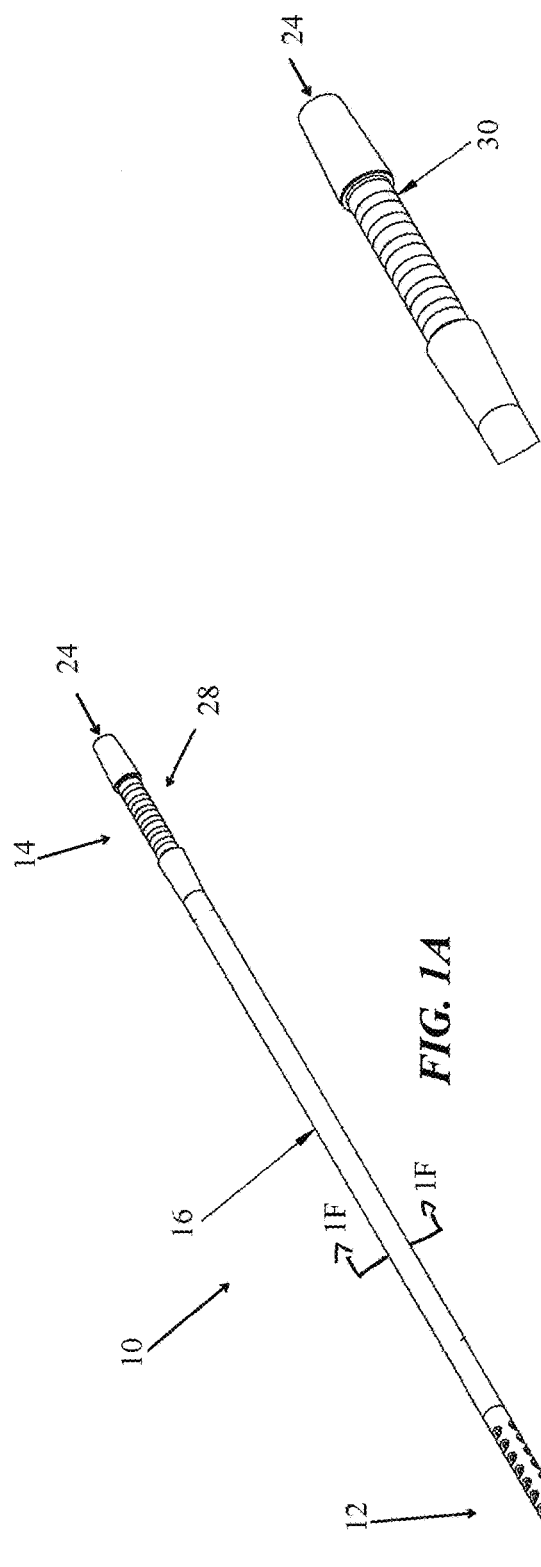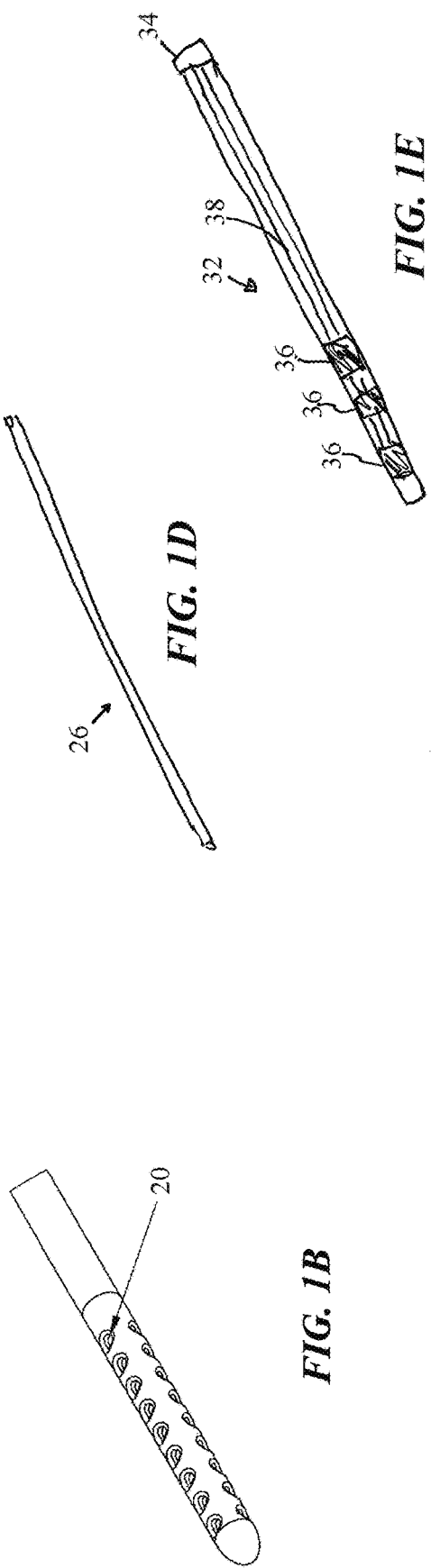

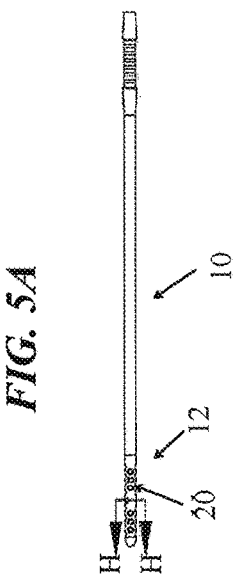
FIG. 5A
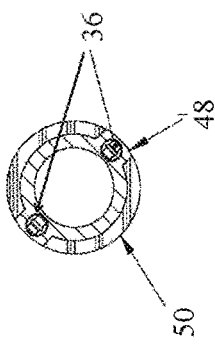
FIG. 5B
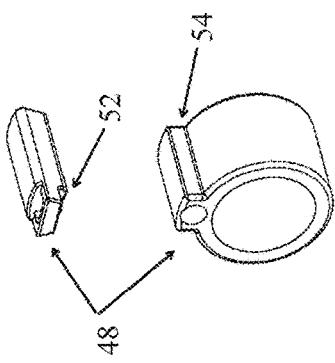
FIG. 6A
FIG. 6B
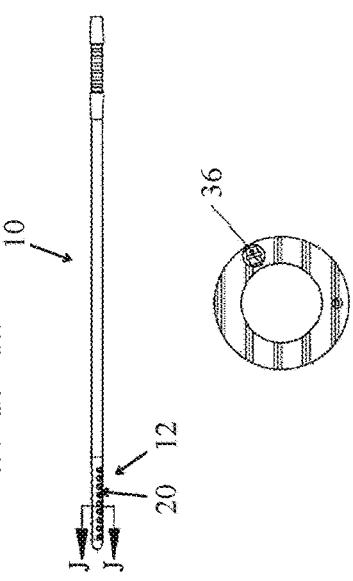
FIG. 4A
FIG. 4B

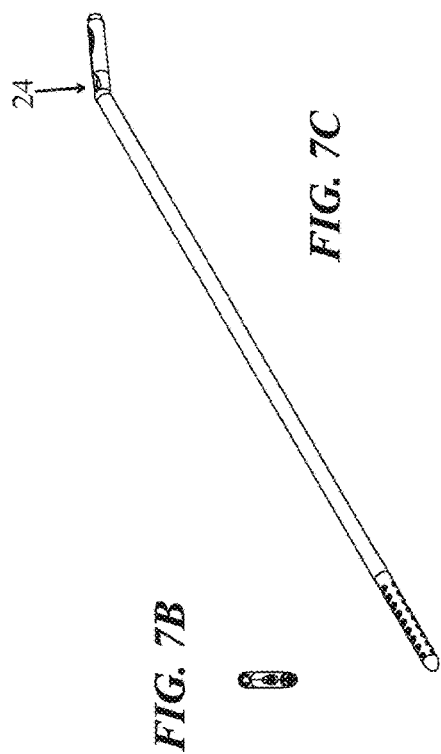
FIG. 7B
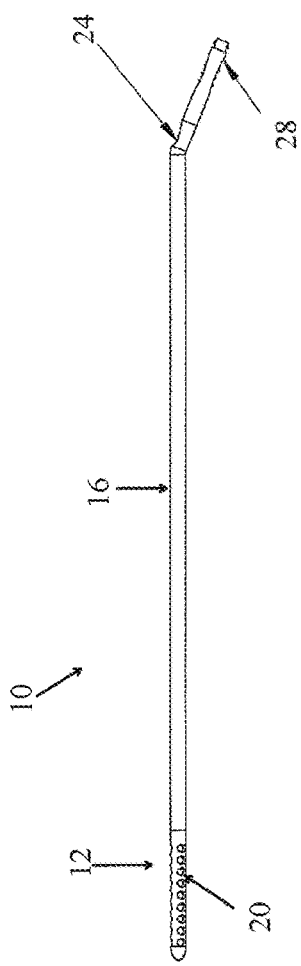
FIG. 7C
FIG. 7A
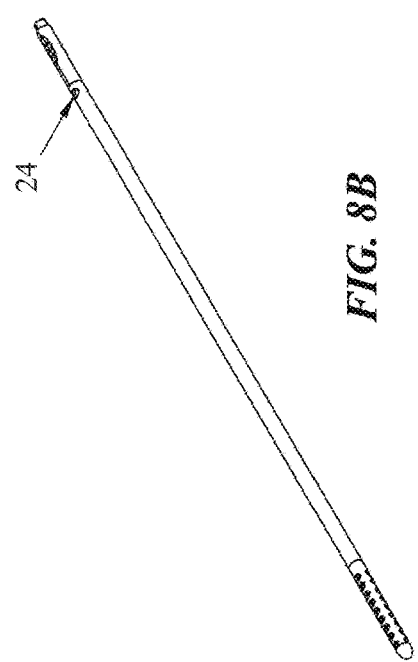
FIG. 8B
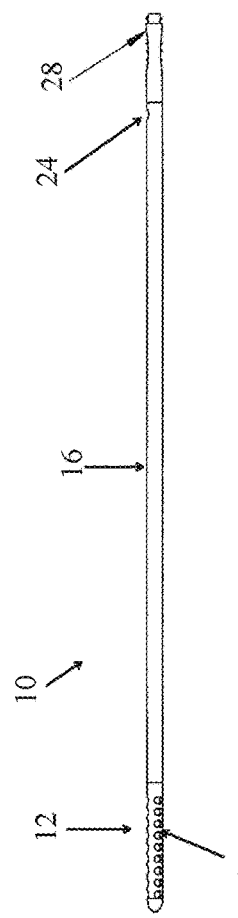
FIG. 8A

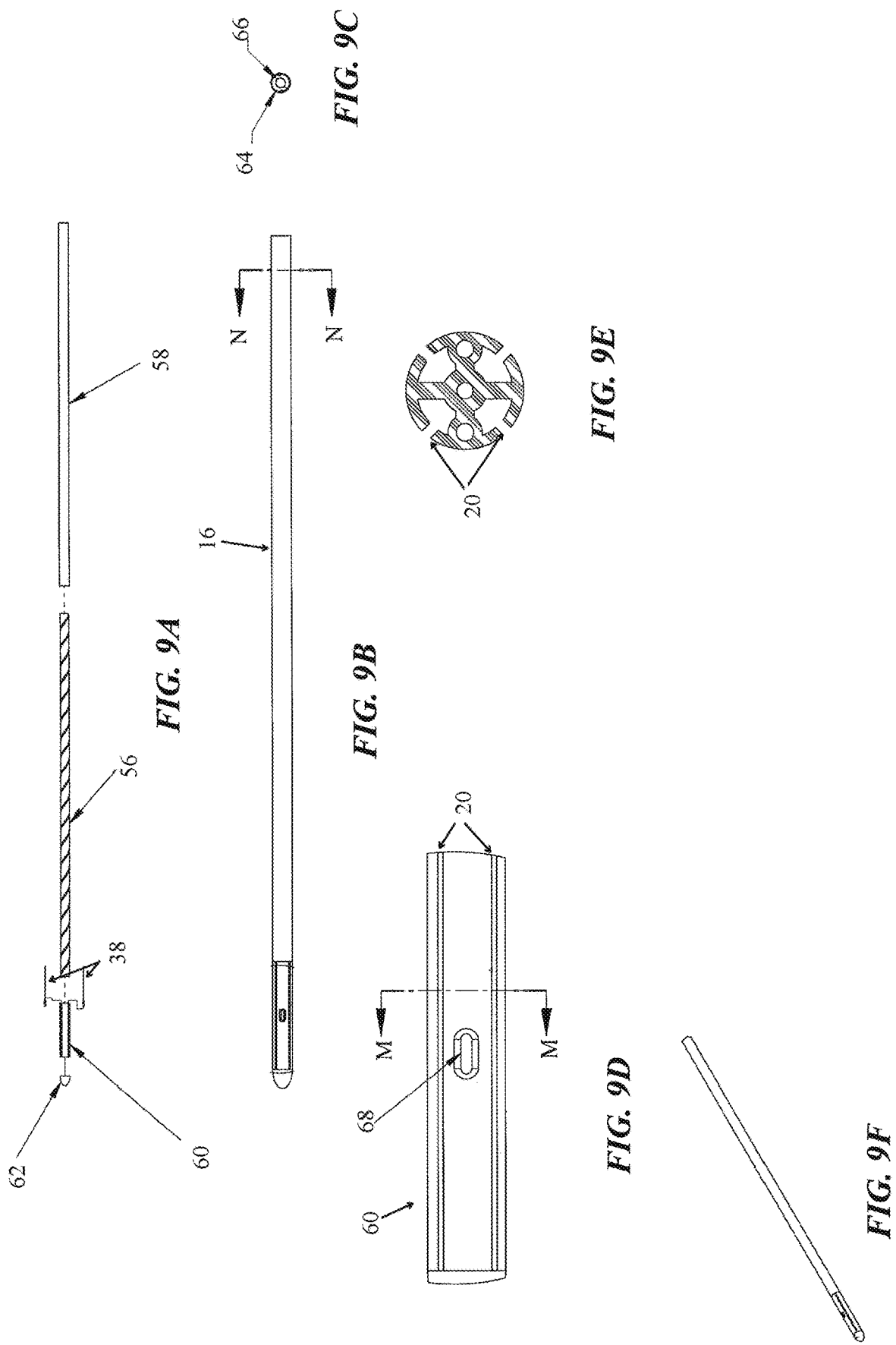

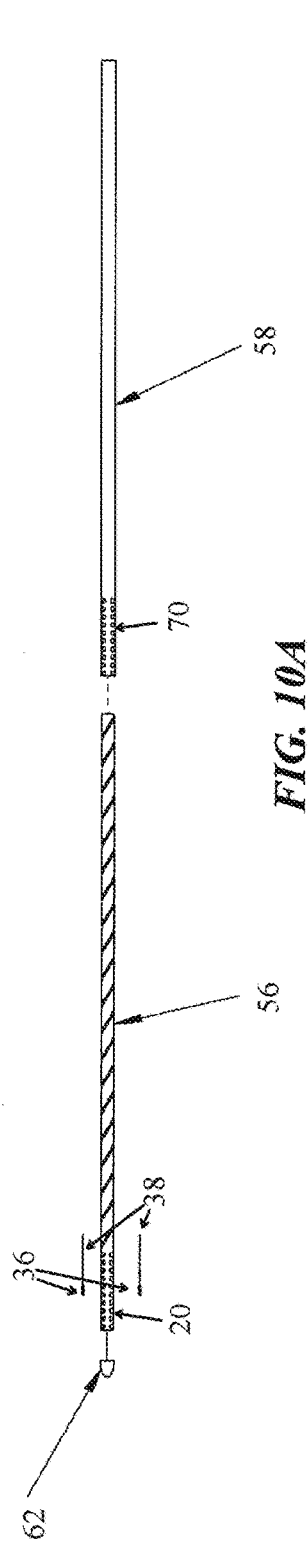
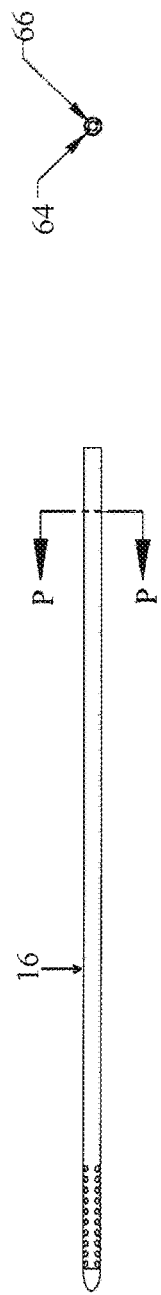
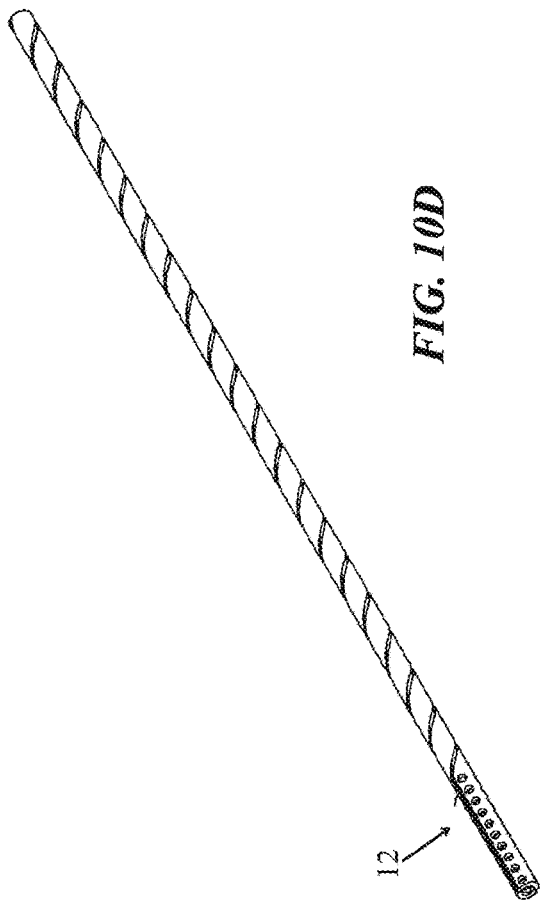
*FIG. 10A*
*FIG. 10B*
*FIG. 10C*
*FIG. 10D*

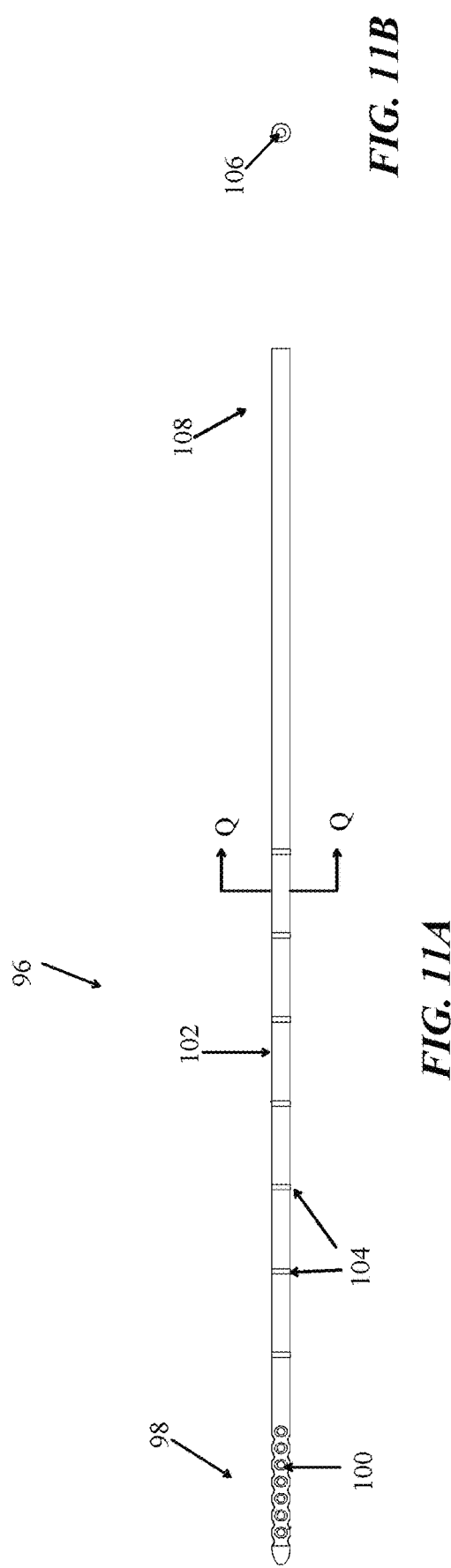
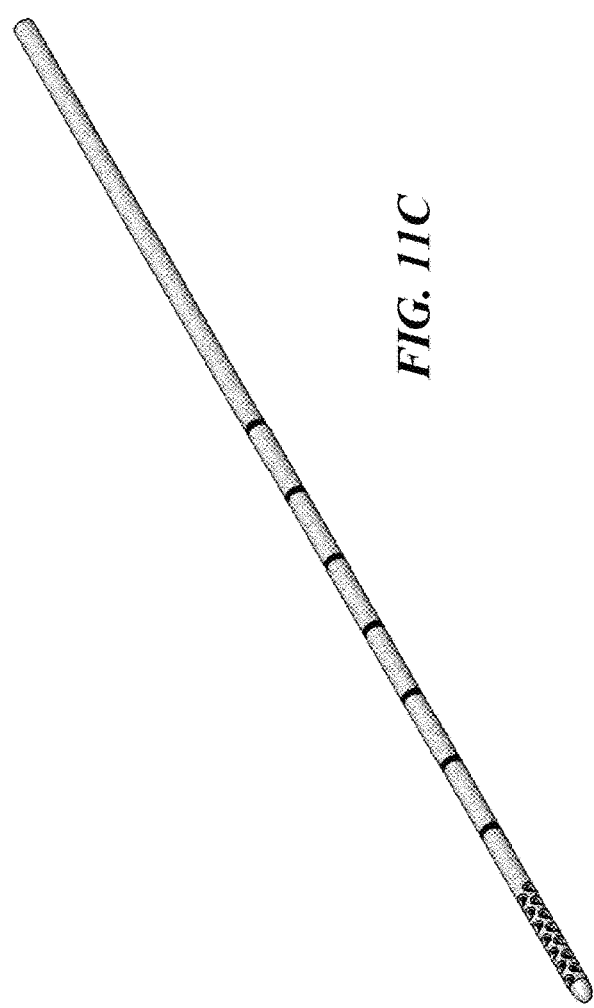

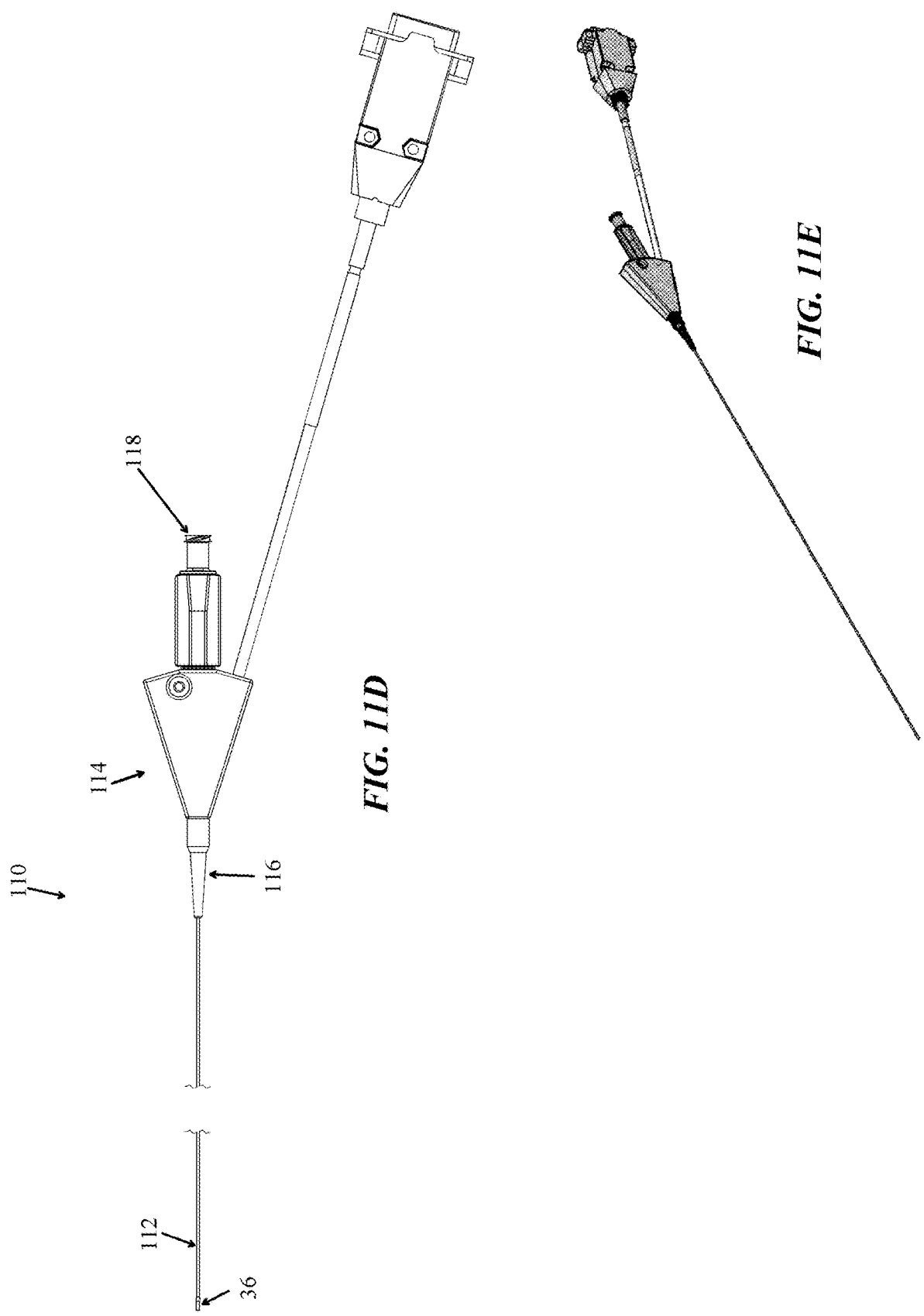

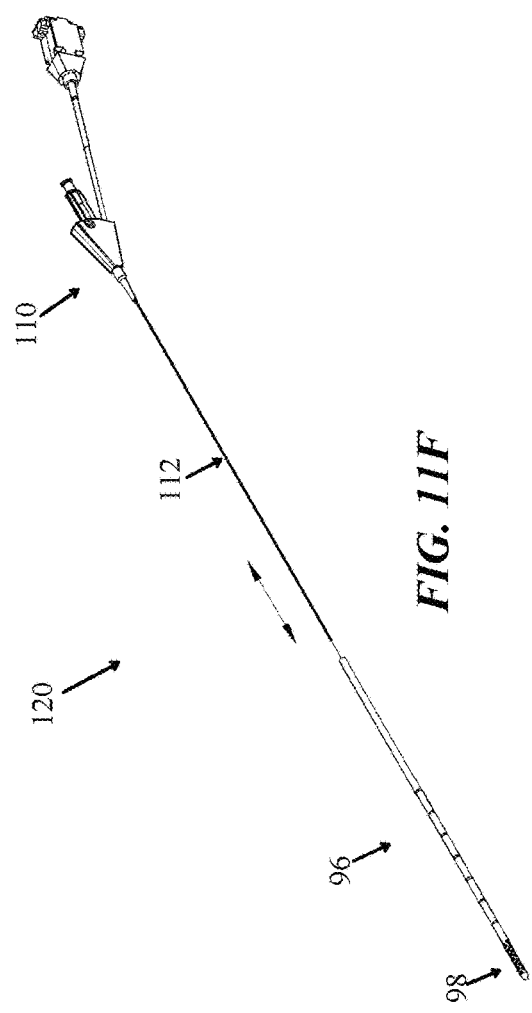
FIG. 11F
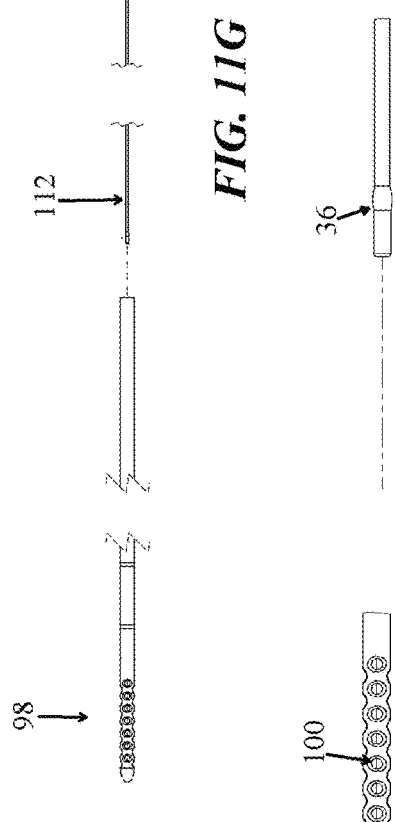
FIG. 11G
FIG. 11H
FIG. 11I

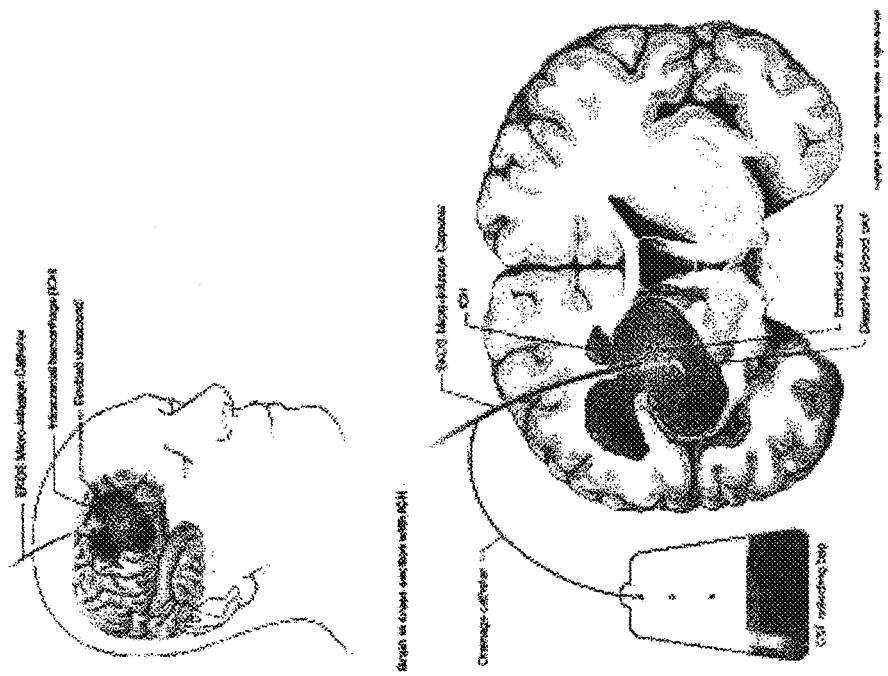
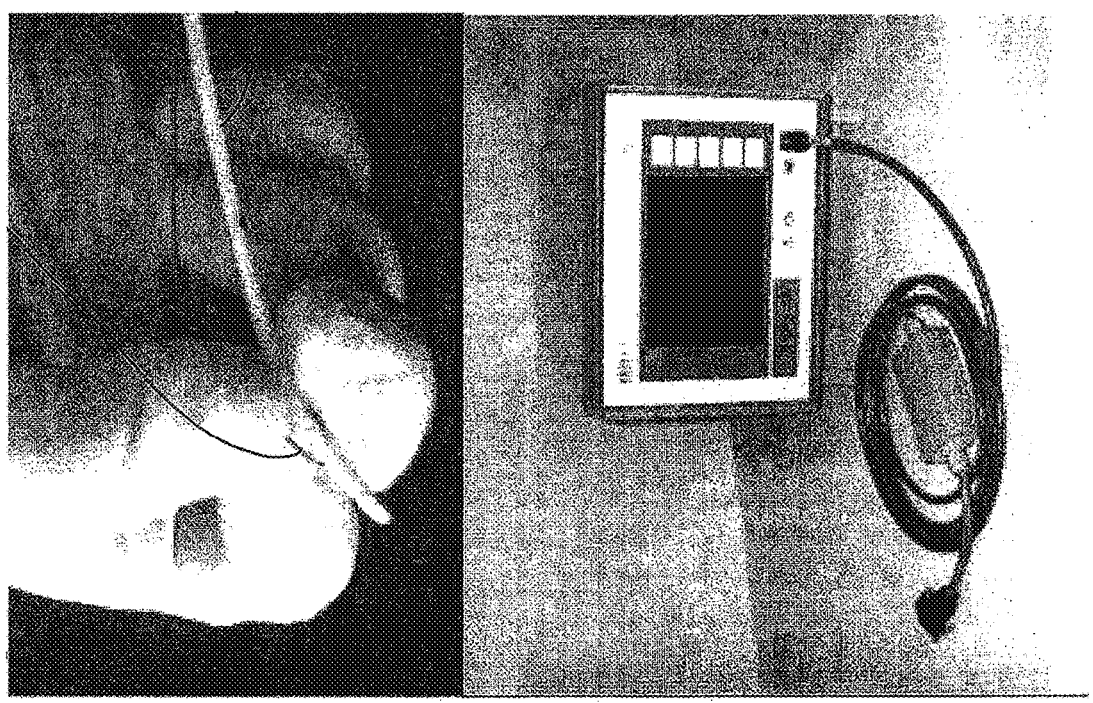
FIG. 15

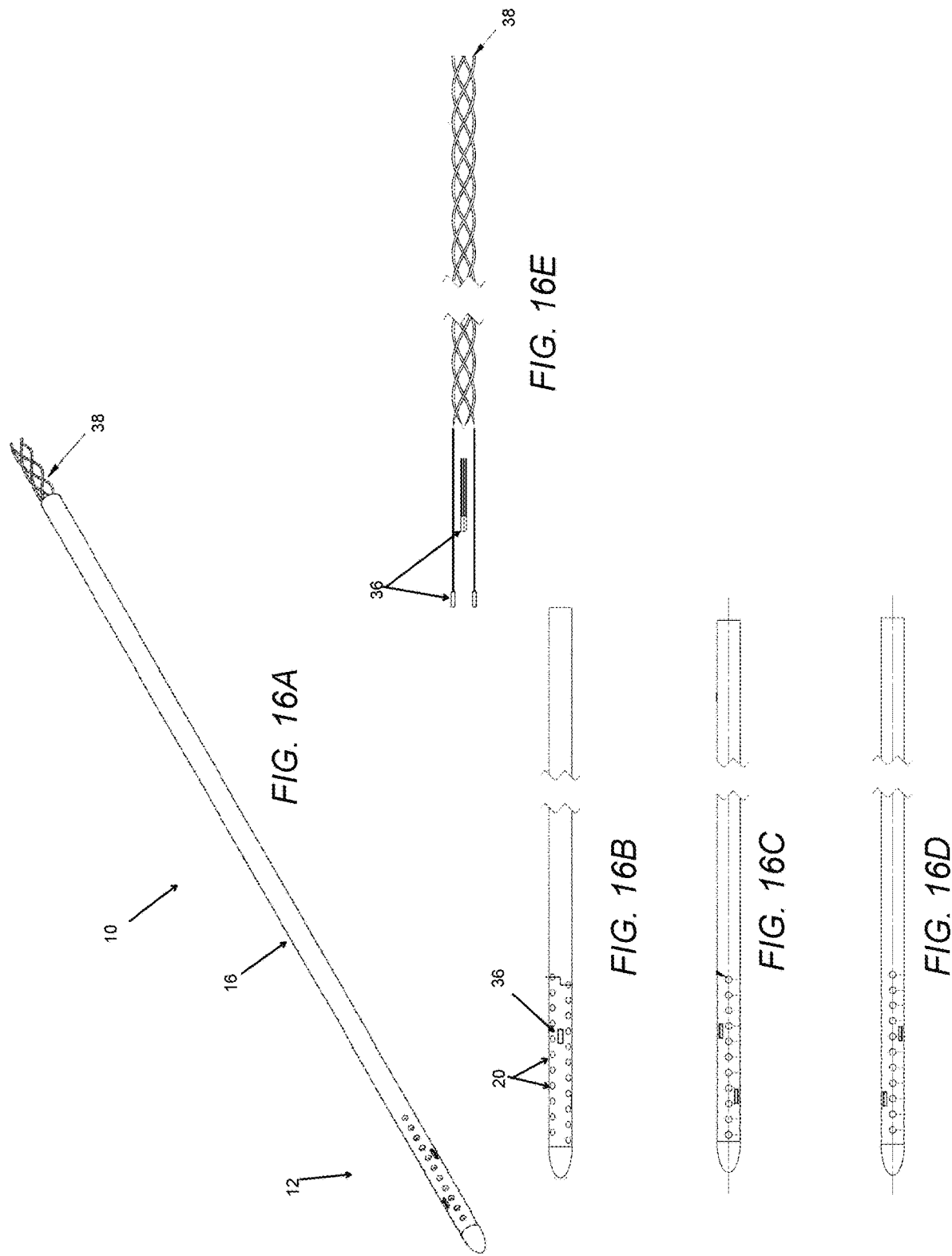

METHOD AND APPARATUS FOR TREATMENT OF INTRACRANIAL HEMORRHAGES

CROSS-REFERENCE TO RELATED APPLICATIONS

This application claims the priority benefit of U.S. Provisional Application No. 61/377,639, filed Aug. 27, 2010, the entire contents of which is hereby incorporated by reference herein.

STATEMENT REGARDING FEDERALLY SPONSORED R&D

The invention was made with government support under Grant No. 1RC3NS070623-01 awarded by the National Institutes of Health and the National Institute of Neurological Disorders and Stroke. The government has certain rights to the invention.

BACKGROUND OF THE INVENTION

Field of the Invention

The present invention relates to methods and apparatuses for the treatment of intracranial hemorrhages, and more specifically, to methods and apparatuses for the treatment of intracranial hemorrhages using an ultrasound.

Background of the Invention

A large number of Americans each year suffer a hemorrhagic stroke. Most of these occur in the basal ganglia, and a third of those include bleeding into the ventricles. Half of these victims will die within months, and a quarter of the survivors will have a second stroke within five years. Bleeding in the brain occurs due to high blood pressure, aneurysms, and less frequently arterio-venous malformations (AVM), and increases in incidence with age. Factors including smoking, diabetes, and obesity play roles, as do amyloid deposits in the elderly.

With respect to stroke treatment, up to a large number of cases per year involve surgical intervention. The objectives of surgical intervention generally include clipping bleeding aneurysms, removing bleeding AVMs, and removing clot volume in intracranial hemorrhages (ICH).

In certain applications, an interventional radiologist will insert Goldvalve detachable balloons, Guglielmi detachable coils, or Onyx liquid embolic to occlude AVMs and saccular aneurysm. These applications are primarily preventive (e.g., preventing a second bleed). Other methods of reducing further bleeding include using embolics and FVIIa, and/or maintaining intracranial pressure below mean arterial pressure. Medical therapy typically also includes head elevation, Tylenol for temperature reduction, paralytics to prevent coughing, intubation to prevent aspiration, Mannitol and diuretics to reduce fluid volume, and seizure preventatives.

Recently, lytics have been considered as a treatment option to remove obstruction in the ventricles and to reduce intracranial pressure. See e.g., U.S. Patent Publication No. 2006/0078555 to Hanely et al. published on Apr. 13, 2006 and filed on Mar. 29, 2003. However, such treatment has not been widely adopted because it is generally considered too slow to provide sufficient clinical benefits. More recently, therapies have been developed that combine ultrasound with a lytic such as recombinant tissue plasminogen activator (rt-PA). In such therapies, the lytic and ultrasound can delivered through a microcatheter directly into spontaneous IVH or ICH patients, to facilitate evacuation of the hemorrhage. See e.g., U.S. Patent Publication No. 2008/0319376 to Wilcox et al. published on Dec. 25, 2008 and filed on Jun. 20, 2008.

While such therapies have shown promise, there is a general desire to continue to improve the methods and apparatuses involved with such therapy.

SUMMARY OF THE INVENTIONS

An embodiment of an ultrasound catheter for treatment of a blood clot resulting from an intracranial hemorrhage comprises an elongate tubular body having a distal portion, a proximal portion, and a central lumen. The catheter further comprises a plurality of ultrasound radiating elements positioned within the tubular body. A plurality of ports are located on the distal portion of the elongate tubular body, and are configured to allow a fluid to flow through the ports.

In another embodiment an ultrasound catheter assembly includes an elongate tubular body having a distal portion and a proximal portion. The elongate tubular body has material properties similar to that of standard external ventricular drainage (EVD) catheter. A lumen is formed within the elongate tubular body. The lumen includes a plurality of ports on the distal portion of the elongate tubular body configured to allow fluid to flow therethrough. An ultrasonic core is configured to be received within the lumen of the catheter. The ultrasonic core comprises a plurality of ultrasound radiating elements.

In another embodiment, an ultrasound catheter comprises an elongate tubular body having a distal portion and a proximal portion. A first drainage lumen is formed within the elongate tubular body. The drainage lumen includes a plurality of drainage ports on the distal portion of the elongate tubular body configured to allow fluid to flow therethrough. A delivery lumen is formed within the elongate tubular body. The delivery lumen includes a plurality of delivery ports on the distal portion of the elongate tubular body configured to allow fluid to flow therethrough. A plurality of ultrasound radiating elements are positioned within the elongate tubular body.

BRIEF DESCRIPTION OF THE DRAWINGS

Exemplary embodiments of the method and apparatus for treatment of intracranial hemorrhages are illustrated in the accompanying drawings, which are for illustrative purposes only. The drawings comprise the following figures, in which like numerals indicate like parts.

FIG. 1A is a schematic illustration of an ultrasonic catheter configured for insertion within the cranial cavity.

FIG. 1B is an enlarged detail view of the distal end of the ultrasonic catheter shown in FIG. 1A.

FIG. 1C is an enlarged detail view of the proximal end of the ultrasonic catheter shown in FIG. 1A.

FIG. 1D is a schematic illustration of a stylet that can inserted into the ultrasonic catheter shown in FIG. 1A.

FIG. 1E is a schematic illustration of ultrasonic core that can inserted into the ultrasonic catheter shown in FIG. 1A.

FIG. 4A is a schematic illustration of an ultrasonic catheter configured for insertion within the cranial cavity.

FIG. 4B is a cross-sectional of the ultrasonic catheter shown in FIG. 4A.

FIG. 5A is a schematic illustration of an ultrasonic catheter configured for insertion within the cranial cavity, according to yet another embodiment FIG. 5B is a cross-sectional view taken of the ultrasonic catheter shown in FIG. 5A.

FIG. 6A is a perspective view of a feature for receiving an ultrasonic element.

FIG. 6B is a perspective view of another embodiment of a feature for receiving an ultrasonic element.

FIG. 7A is a schematic illustration of an ultrasonic catheter with a coaxial drain port.

FIG. 7B is an axial view of the ultrasonic catheter shown in FIG. 7A.

FIG. 7C is a perspective view of the ultrasonic catheter of FIG. 7A.

FIG. 8A is a schematic illustration of an ultrasonic catheter with drain ports proximal to the connector.

FIG. 8B is a perspective view of the ultrasonic catheter of FIG. 8A.

FIG. 9A is an exploded view of an ultrasonic catheter, according to an embodiment.

FIG. 9B is a schematic illustration of the ultrasonic catheter shown in FIG. 9A.

FIG. 9C is a cross-sectional view of the tubular body of the ultrasonic catheter shown in FIG. 9B.

FIG. 9D is an enlarged detail view of the distal end of the ultrasonic catheter shown in FIG. 9B.

FIG. 9E is a cross-sectional view of the distal extrusion of the ultrasonic catheter shown in FIG. 9D.

FIG. 9F is a perspective view of the ultrasonic catheter shown in FIG. 9B

FIG. 10A is an exploded view of an ultrasonic catheter, according to another embodiment.

FIG. 10B is a schematic illustration of the ultrasonic catheter shown in FIG. 10A.

FIG. 10C is a cross-sectional view of the ultrasonic catheter shown in FIG. 10B.

FIG. 10D is a perspective view of the spiral extrusion shown in FIG. 10A.

FIG. 11A is a schematic view of a drain, according to one embodiment.

FIG. 11B is a cross-sectional view of the drain shown in FIG. 11A.

FIG. 11C is a perspective view of the drain shown in FIG. 11A.

FIG. 11D is a schematic view of an ultrasonic core, according to one embodiment.

FIG. 11E is a perspective view of the ultrasonic core shown in FIG. 11D.

FIG. 11F is a perspective view of a catheter assembly, according to one embodiment.

FIG. 11G is a schematic view of the catheter assembly shown in FIG. 11F.

FIG. 11H is an enlarged detail view of the distal end of the drain shown in FIG. 11A.

FIG. 11I is an enlarged detail view of the distal end of the ultrasonic core shown in FIG. 11D.

FIG. 15 is a table listing certain features of various embodiments of an ultrasonic catheter.

FIG. 16A is a perspective view of an ultrasonic catheter, according to another embodiment.

FIGS. 16B-D are enlarged detail views of the distal portion of the ultrasonic catheter shown in FIG. 16A. is a schematic illustration of the ultrasonic catheter shown in FIG. 10A.

FIG. 16E is a schematic illustration of wires and ultrasonic radiating members embedded within the ultrasonic catheter shown in FIG. 16A.

DETAILED DESCRIPTION OF THE PREFERRED EMBODIMENTS

Figure 1F:
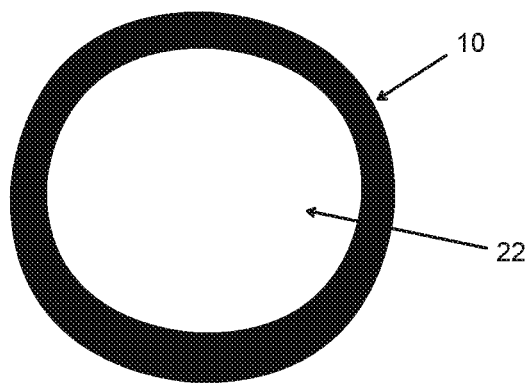
FIG. 1F is cross-sectional view taken through line 1F-1F of FIG. 1A.

As set forth above, methods and apparatuses have been developed that allow an intracranial hemorrhage and/or a subarachnoid hemorrhage to be treated using ultrasonic energy in conjunction with a therapeutic compound. As used herein, the term "intracranial hemorrhage" encompasses both intracerebral hemorrhage and intraventricular hemorrhage. Although some embodiments may be disclosed with reference to intracerebral hemorrhage or intraventricular hemorrhage, the embodiments can generally be used to treat both types of intracranial hemorrhages. Disclosed herein are several exemplary embodiments of ultrasonic catheters that can be used to enhance the efficacy of therapeutic compounds at a treatment site within a patient's body. Also disclosed are exemplary methods for using such catheters. For example, as discussed in greater detail below, the ultrasonic catheters disclosed herein can be used to deliver a therapeutic compound to a blood clot in the brain, allowing at least a portion of the blood clot to be dissolved and/or removed, thereby reducing damage to brain tissue. Although described with respect to intracranial use, the embodiments disclosed herein are also suitable for intraventricular use in other applications. Accordingly, the term "intracranial use" can also include intraventricular use.

As used herein, the term "therapeutic compound" refers broadly, without limitation, and in addition to its ordinary meaning, to a drug, medicament, dissolution compound, genetic material or any other substance capable of effecting physiological functions. Additionally, a mixture including substances such as these is also encompassed within this definition of "therapeutic compound". Examples of therapeutic compounds include thrombolytic compounds, anti-thrombosis compounds, and other compounds used in the treatment of vascular occlusions and/or blood clots, including compounds intended to prevent or reduce clot formation, neuroprotective agents, anti-apoptotic agents, and neurotoxin scavenging agents. Exemplary therapeutic compounds include, but are not limited to, heparin, urokinase, streptokinase, tPA, rtPA, BB-10153 (manufactured by British Biotech, Oxford, UK), plasmin, IIbIIa inhibitors, desmoteplase, caffeinol, deferoxamine, and factor VIIa.

As used herein, the terms "ultrasonic energy", "ultrasound" and "ultrasonic" refer broadly, without limitation, and in addition to their ordinary meaning, to mechanical energy transferred through longitudinal pressure or compression waves. Ultrasonic energy can be emitted as continuous or pulsed waves, depending on the parameters of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy referred to herein has a frequency between about 20 kHz and about 20 MHz. For example, in one embodiment, the ultrasonic energy has a frequency between about 500 kHz and about 20 MHz. In another embodiment, the ultrasonic energy has a frequency between about 1 MHz and about 3 MHz. In yet another embodiment, the ultrasonic energy has a frequency of about 2 MHz. In certain embodiments described herein, the average acoustic power of the ultrasonic energy is between about 0.01 watts and 300 watts. In one embodiment, the average acoustic power is about 15 watts.

As used herein, the term "ultrasound radiating element" or "ultrasound or ultrasonic element" refers broadly, without limitation, and in addition to its ordinary meaning, to any apparatus capable of producing ultrasonic energy. An ultrasonic transducer, which converts electrical energy into ultrasonic energy, is an example of an ultrasound radiating element. An exemplary ultrasonic transducer capable of generating ultrasonic energy from electrical energy is a piezoelectric ceramic oscillator. Piezoelectric ceramics typically comprise a crystalline material, such as quartz, that changes shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating element, and the ultrasonic energy can be transmitted, via, for example, a wire that is coupled to the ultrasound radiating element. In such embodiments, a "transverse wave" can be generated along the wire. As used herein is a wave propagated along the wire in which the direction of the disturbance at each point of the medium is perpendicular to the wave vector. Some embodiments, such as embodiments incorporating a wire coupled to an ultrasound radiating element for example, are capable of generating transverse waves. See e.g., U.S. Pat. Nos. 6,866,670, 6,660,013 and 6,652,547, the entirety of which are hereby incorporated by reference herein. Other embodiments without the wire can also generate transverse waves along the body of the catheter.

In certain applications, the ultrasonic energy itself provides a therapeutic effect to the patient. Examples of such therapeutic effects include blood clot disruption; promoting temporary or permanent physiological changes in intracellular or intercellular structures; and rupturing micro-balloons or micro-bubbles for therapeutic compound delivery. Further information about such methods can be found in U.S. Pat. Nos. 5,261,291 and 5,431,663.

Figure 1G:
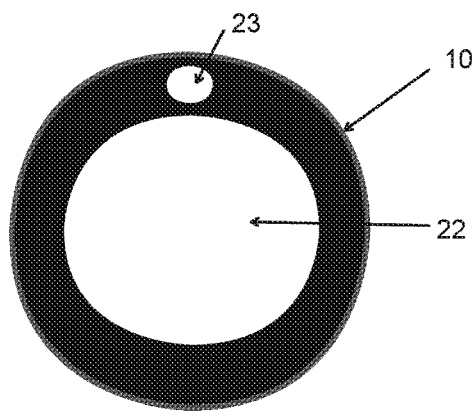
FIG. 1G is a cross-sectional view of an ultrasonic catheter, according to an embodiment.
Figure 1H:
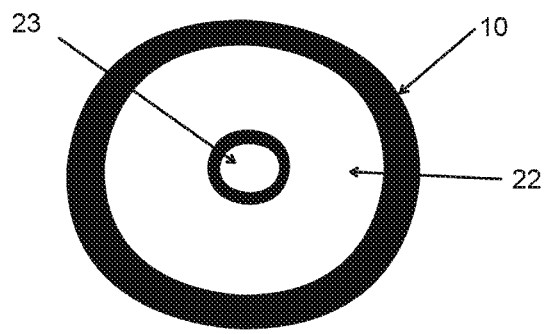
FIG. 1H is a cross-sectional view of an ultrasonic catheter, according to another embodiment.

FIGS. 1A to 1C and FIG. 1F schematically illustrate one arrangement of an ultrasonic catheter 10 that can be used to treat a blood clot in the brain resulting from an intracerebral hemorrhage (ICH) and/or an intraventricular hemorrhage (IVH). FIG. 1B shows an enlarged detail view of a distal portion 12 of the catheter 10 and FIG. 1C illustrates an enlarged detail view of a proximal portion 14 of the catheter 10. In the illustrated arrangement, the ultrasonic catheter 10 generally includes a multi-component, elongate flexible tubular body 16 having a proximal region 14 and a distal region 12. The tubular body 16 includes a flexible energy delivery section 18 located in the distal region 12. Within the distal region 12 are located a plurality of holes 20, through which fluid may flow into or out of a central lumen 22 (FIG. 1F) that extends through the catheter 10. Although the drainage holes 20 are shown as circular, the shape of the holes may be varied. For instance, the drainage holes may be oval, polygonal, or irregular. FIGS. 1G and 1H illustrate modified embodiments of the catheter which include separate lumens for fluid delivery and for fluid evacuation.

The catheter 10 defines the hollow lumen 22 which allows for the free flow of liquids between the drainage holes 20 and the proximal port 24. For instance, blood may flow from an area external to the ultrasonic catheter through the drainage holes 20 and into the lumen 22. The blood may then flow proximally in the lumen 22 towards the proximal region 14 of the ultrasonic catheter, where it may be collected via the drainage kit. In certain embodiments, any number of therapeutic compounds may be introduced into the ultrasonic catheter through the proximal end 14. The compounds, which may be dissolved or suspended within a liquid carrier, may flow through the lumen 22 and towards the distal end 12 of the ultrasonic catheter, ultimately exiting the catheter through drainage holes 20 and entering a treatment site.

In certain embodiments, negative pressure may be applied to the lumen 22 of the catheter to facilitate the flow of blood from the drainage holes 20 towards the proximal end 14. In other embodiments, no external pressure is applied, and the conditions present at the treatment site are sufficient to cause the blood to flow proximally through the lumen 22. In some embodiments, a positive pressure may be applied to the lumen 22 of the catheter 10 in order for therapeutic compounds or other liquids to pass distally through the lumen 22 towards the drainage holes 20. In other embodiments, no external pressure is applied, and the liquid is permitted to independently flow distally and exit the drainage ports 20.

The tubular body 16 and other components of the catheter 10 can be manufactured in accordance with a variety of techniques known to an ordinarily skilled artisan. Suitable materials and dimensions can be readily selected based on the natural and anatomical dimensions of the treatment site and on the desired access site. In addition, the surface of the catheter 10 can be coated with an antimicrobial material, such as silver or a silver based compound. In certain embodiments, the catheter may be biocompatible for use in the brain for up to 7 days, for up to 15 days, up to 29 days, or for up to 35 days. In one arrangement, the catheter can be coated with a hydrophilic material.

In some embodiments, the tubular body 16 can be between about 23 and 29 centimeters in length. In certain arrangements, the lumen 22 has a minimum inner diameter of about 2 millimeters and the catheter body has a maximum outer diameter of about 6 mm.

In one particular embodiment, the tubular body 16 has material properties similar to that of standard external ventricular drainage (EVD) catheters. For example, the tubular body can be formed of radiopaque polyurethane or silicone, which can be provided with antimicrobial features. In such embodiments, the catheter 10 by itself may not have sufficient flexibility, hoop strength, kink resistance, rigidity and structural support to push the energy delivery section 18 through an opening in the skull and then, in turn, the patient's brain tissue to a treatment site (e.g., one of the ventricles). Accordingly, the catheter 10 can be used in combination with a stylet 26 (FIG. 1D), which can be positioned within the tubular body 10. In one embodiment, the device is configured to be compatible with Neuronavigation systems by easily accommodating the Neuronavigation system stylet. The stylet 26 can provide additional kink resistance, rigidity and structural support to the catheter 10 such that it can be advanced through the patients' brain tissue to the target site. In certain embodiments, the stylet 26 can be configured to be used in combination with a standard image guided EVD placement system. As described below, after placement, the stylet 26 can then be removed to allow drainage through the tubular body 16. In a modified arrangement, the tubular body 16 can be reinforced by braiding, mesh or other constructions to provide increased kink resistance and ability to be pushed with or without a stylet.

In one embodiment, the tubular body energy delivery section 18 can comprise a material that is thinner than the material comprising the tubular body proximal region 14. In another exemplary embodiment, the tubular body energy delivery section 18 comprises a material that has a greater acoustic transparency than the material comprising the tubular body proximal region 14. In certain embodiments, the energy delivery section 18 comprises the same material or a material of the same thickness as the proximal region 14.

FIG. 1C shows an enlarged detail view of the proximal portion 14 of the ultrasonic catheter 10. The proximal portion 14 includes a connector 28. In the embodiment shown, the connector 28 comprises a series of annular rings 30 aligned in parallel. The connector 28 permits the catheter 10 to be joined to a drainage kit. For example, in one arrangement, the connector 28 is configured to connect to a standard EVD drainage kit that can include an attachment fitting that slides over the connector 28 or can include a buckle or joint that is fastened around connector 28. Specific length and configuration of the connector 28 can vary according to the needs of the particular application, and to facilitate connection with various drainage kits. Additionally, the number of annular rings 30 may vary in certain embodiments.

In the illustrated arrangement of FIGS. 1A-D and 1F, the catheter 10 can be use in combination with an inner core 32 (FIG. 1E) which can be inserted into the lumen 22 after the stylet 26 has been removed to deliver ultrasound energy to the target site. The core 32 can include proximal hub 34 fitted on one end of the inner core 32 proximal region. One or more ultrasound radiating members 36 are positioned within a distal region of the core and are coupled by wires 38 to the proximal hub 34. In some embodiments, the inner core 32 can be inserted into the lumen 22 and/or along a side of the catheter 10. In yet another arrangement, the core 32 can be inserted into the lumen 22 with the distal end including the ultrasound radiating members extending outside one of the holes positioned on the distal region of the catheter 10.

In other embodiments, the catheter 10 can include separate lumens for drainage and for drug delivery. FIGS. 1G and 1H show cross-sectional views of two embodiments of a catheter with multiple lumens. With reference to FIG. 1G, a fluid-delivery lumen 23 is located within the wall of the catheter 10, between the outer surface and the inner lumen 22, which may be used for fluid evacuation. In other embodiments, a plurality of fluid-delivery lumens 23 may be arranged within the catheter 10. Although shown as substantially circular in cross-section, any number of shapes may be employed to provide for optimal fluid flow through the fluid-delivery lumen 23. With reference to FIG. 1H, a separate fluid-delivery lumen 23 is located within a separate tube running longitudinally within the inner lumen 22. In certain embodiments, a plurality of fluid-delivery lumens 23 may be arranged within inner lumen 22. The size of fluid-delivery lumen 23 may be small enough so as to not interfere with the function of inner lumen 23 in evacuating fluid from the treatment site.

These separate lumens connect drainage and drug delivery holes positioned generally at the distal end of the catheter with drug delivery and drainage ports positioned at the proximal end of the catheter. In one embodiment, the device can include separate lumens for the drug and drain delivery such that the holes and ports for drug delivery and drainage are separated from each other. In some embodiments, the treatment zone (defined as the distance between the distal most and proximal most ultrasound transducer) can be about 1 to 4 cm. In other embodiments, the treatment zone may extend as far as 10 cm. The drug and drain ports can include luer type fittings. The ultrasound transducers can be positioned near or between the drain and drug delivery holes.

FIGS. 2A-D are schematic illustrations of an ultrasonic catheter according to another embodiment. The catheter 10 contains components similar to that shown in FIGS. 1A-C and FIG. 1F-H. However, in this embodiment, includes wires 38 embedded within the wall of the tube. As will be explained below, the wires can activate and control ultrasonic radiating elements located within the distal region 12 of the catheter 10. Additionally, the catheter 10 may include thermocouples for monitoring temperature of the treatment zone, the catheter, or surrounding areas. In some embodiments, each ultrasound radiating element is associated with a temperature sensor that monitors the temperature of the ultrasound radiating element. In other embodiments, the ultrasound radiating element itself is also a temperature sensor and can provide temperature feedback. In certain embodiments, one or more pressure sensors are also positioned to monitor pressure of the treatment site or of the liquid within the lumen of the catheter.

In the embodiment shown, the wires 38 are bundled and embedded within the wall of the tubular body 16. In other embodiments, the wires may not be bundled, but may, for example, each be spaced apart from one another. Additionally, in certain embodiments the wires may not be embedded within the wall of the tubular body 16, but may rather run within the lumen 22. The wires 38 may include protective and/or insulative coating.

The wires may be advantageously configured such that they can withstand tension applied to the catheter. For example, the wires may be able to withstand at least 3 pounds of tension. In other embodiments, the wires may be able to withstand at least 3.6 pounds, at least 4 pounds, or at least 4.5 pounds of tension.

The wires may also be configured such that they increase the stiffness of the tubular body 16 as little as possible. The flexibility of the tubular body 16 facilitates the introduction of the catheter 10 into the cranial cavity. It may therefore be advantageous to select wires that only minimally contribute to the stiffness of the catheter. The wires chosen may be between 30 and 48 gauge. In other embodiments, the wires may be between 33 and 45 gauge, between 36 and 42 gauge, or between 38 and 40 gauge. The number of wires within the catheter is determined by the number of elements and thermocouples in a particular device.

Figure 2D:
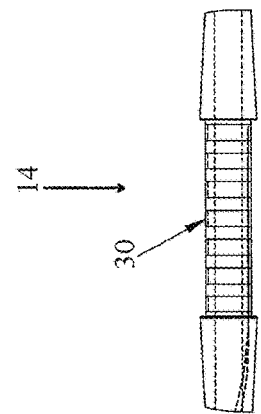
FIG. 2D is an enlarged detail view of the proximal end of the ultrasonic catheter shown in FIG. 2A.
Figure 2A:
FIG. 2A is a schematic illustration of an ultrasonic catheter with embedded wires.
Figure 2C:
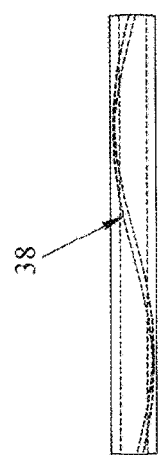
FIG. 2C is an enlarged detail view of a medial portion of the ultrasonic catheter shown in FIG. 2A.
Figure 2B:
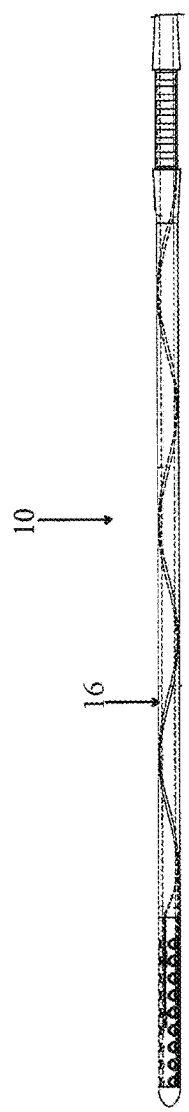
FIG. 2B is an enlarged detail view of the distal end of the ultrasonic catheter shown in FIG. 2A.

In certain embodiments, the drainage holes 20 include radii on the outside of the holes, as can be seen in FIG. 2B. Applying a larger external radius to each drainage hole may improve the flow of blood into the drainage holes 20 and through the lumen of the catheter and may reduce damage to brain tissue during insertion and withdrawal. Although the drainage holes 20 are depicted as arranged in regular rows, the pattern may vary considerably. The length of the region in which the holes are located may be between 2 and 4 cm. In certain embodiments, the length may be between 2.5 and 3.5 cm, or the length may be about 3 cm.

In the embodiment shown, the annular rings 30 located within in the proximal region 14 of the catheter 10 may be connected to the wires 38. In certain embodiments, a wire may be soldered to each annular ring 30. An electrical contact may then be exposed on the outer diameter of the annular ring 30 to provide for an electrical connection to an individual wire. By virtue of this design, each wire, and therefore each thermocouple or element, may be addressed independently. In alternative embodiments, two or more wires may be soldered to an annular ring, thereby creating a single electrical connection. In other embodiments, the wires may meet electrical contacts at other points within the catheter 10. Alternatively, the wires may pass through the wall of the tubular body 16 and connect directly to external apparatuses.

Figure 3:
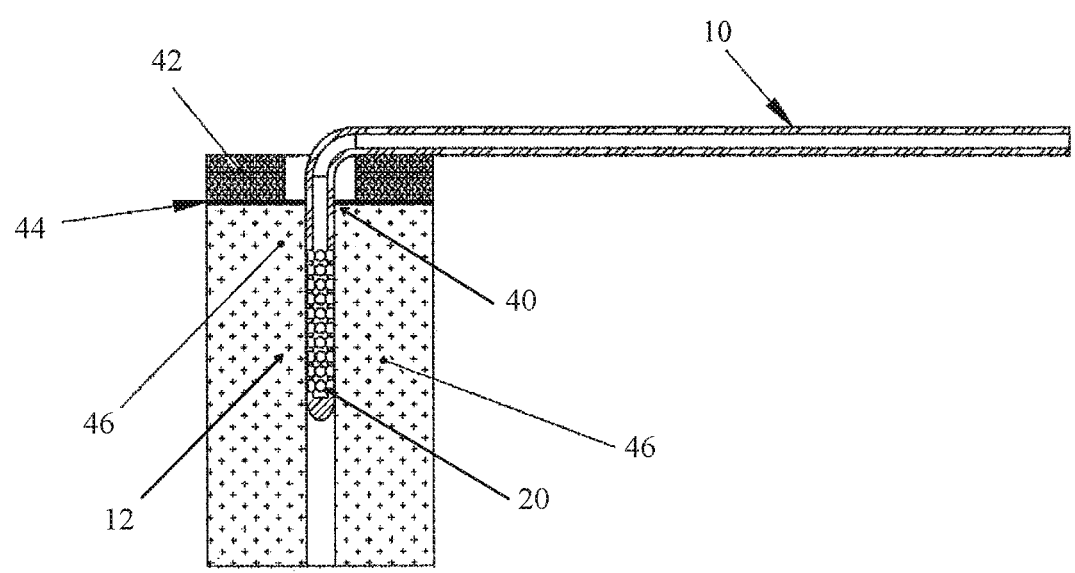
FIG. 3 is a schematic illustration of an ultrasonic catheter partially inserted into the brain.

FIG. 3 is a schematic illustration of an ultrasonic catheter partially inserted into the brain. The catheter 10 may be positioned against the external surface of the skull, with the distal portion inserted through bore 40. The bore 40 creates an access path through the skull 42, dura 44, and into the brain tissue 46. Once in the brain tissue 46, excess blood resulting from hemorrhaging may be accepted into the drainage holes 20 located on the distal region of the catheter. Due to the angle of entry into the brain, the tubular body 16 of the catheter 10 is advantageously kink resistant, in particular around a bend. Kink resistance is advantageous at the distal region 12 of the catheter 10. As the catheter 10 is withdrawn from the brain tissue 46 and begins to straighten, excess stiffness of the catheter can result in the distal tip migrating into the brain tissue 46. The presence of the drainage holes 20 contributes to the flexibility at the distal region 12 of the catheter 10.

In one embodiment, the device can be placed using a tunneling technique which involves pulling the device under the scalp away from the point of entry in the brain to reduce the probability of catheter-initiated infections. In one embodiment, the catheter is made (at least partially) of a soft and pliant silicone material (and/or similar material) which will move with the brain matter during therapy without causing injury.

Dimensions of an ultrasonic catheter may vary according to different embodiments. For example, the Wall Factor is defined as the ratio of the outer diameter of the tube to the wall thickness. The inventors have discovered that a Wall Factor of 4 is useful in preventing kinking of the catheter. In particular, a Wall Factor of 4 may prevent kinking of the catheter around a 10 mm diameter bend, with the bend measured through the centerline of the catheter. The area of the tubular body 16 in which kink resistance is most advantageous is between 5 and 12 cm from the distal end of the device.

Various methods may be employed to impart kink resistance to the catheter 10. For instance, the tubular body 16 may be reinforced with coil to prevent kinking of the catheter around bends. In other embodiments, the tubular body has a wall thickness that is chosen (in light of the material) sufficient to prevent kinking as the catheter is placed through a bend.

FIGS. 4A-B illustrates one arrangement of the ultrasonic radiating elements 36. FIG. 4B is an enlarged detailed view of a cross-section of the ultrasonic catheter shown in FIG. 4A. As shown, in one arrangement, the ultrasonic radiating elements 36 can be disposed in the distal region 12 of the ultrasonic catheter 10. In other embodiments, thermocouples, pressure sensors, or other elements may also be disposed within the distal region 12. The distal region 12 may be composed of silicone or other suitable material, designed with drainage holes 20 as discussed above. Ultrasonic radiating elements 36 may be embedded within the wall of the distal region 12, surrounded by the silicone or other material. In addition to the ultrasonic radiating elements 36, the catheter may include wiring embedded within the wall of the flexible tubular body, as discussed in more detail above with reference to FIGS. 2A-2D. The ultrasonic radiating elements 36 can include connective wiring, discussed in greater detail below. In various embodiments, there may be as few as one and as many as 10 ultrasonic radiating elements 36 can be embedded with the distal region 12 of the device. The elements 36 can be equally spaced in the treatment zone. In other embodiments, the elements 36 can be grouped such that the spacing is not uniform between them. In an exemplary embodiment, the catheter 10 includes two ultrasonic radiating elements 36. In this two-element configuration, the elements can be spaced apart approximately 1 cm axially, and approximately 180 degrees circumferentially. In another embodiment, the catheter 10 includes three ultrasonic radiating elements 36. In this three-element configuration, the elements 36 can be spaced approximately 1 cm apart axially, and approximately 120 degrees apart circumferentially. As will be apparent to the skilled artisan, various other combinations of ultrasonic radiating elements are possible.

FIGS. 5A-B illustrates another arrangement of the distal region of an ultrasonic catheter 10. FIG. 5B is an enlarged detail view of a cross-section of the ultrasonic catheter shown in FIG. 5A. In the configuration shown, two elements are spaced approximately 180 degrees apart circumferentially, and are equidistant from the distal tip of the catheter 10. The catheter can include only two ultrasonic radiating elements 36 in the distal region 12, or alternatively it may include four, six, eight, or more, with each pair arranged in the configuration shown. In embodiments containing more than one pair, the pairs may be aligned axially. Alternatively, each pair may be rotated slightly with respect to another pair of elements. In certain embodiments, each pair of radiating elements 36 are spaced apart axially approximately 1 cm.

Still referring to FIG. 5B, an epoxy housing 48 is shown, surrounded by an external layer of silicone 50. In the embodiment shown, the ultrasonic radiating elements 36 are potted in the epoxy housing 48. The epoxy may be flush with the outer diameter of silicone 50. The epoxy housing 48 may have an axial length less than the length of the distal region 12. In embodiments including multiple pairs of ultrasonic radiating elements 36, each pair of elements may be confined to a separate epoxy housing 48. In one embodiment, the epoxy housing 48 may have an axial length of between 0.75 and 0.2 inches. In other embodiments, the epoxy housing 48 may have an axial length of between 0.1 and 0.15 inches, between 0.11 and 0.12 inches, or approximately 0.115 inches.

FIGS. 6A-B show two embodiments of epoxy housings 48 in which an ultrasonic radiating element 36 may be housed. Although the housing depicted is made from epoxy, any suitable material may be used. For instance, the housing may be made from rubber, polyurethane, or any polymer of suitable flexibility and stiffness. In embodiments employing epoxy, the housing may be formed by filling a polyimide sleeve with epoxy followed by curing.

In some embodiments, epoxy housings 48 may be embedded in the silicone layer with the assistance of chemical adhesives. In other embodiments, the housings 48 may additionally contain structural designs to improve the stability of the housing within the silicone. For instance, the housing 48 shown in FIG. 6A contains a notch 52 which, when fitted with a complementary structure of a silicone layer, may improve the stability of the housing 48 within the silicone layer. Such structural designs may be used in conjunction with or independently of chemical adhesives. FIG. 6B shows another embodiment of an epoxy housing 48. In this embodiment, the raised ridge 54 is designed such that the top surface may lie flush with a silicone layer that surrounds the epoxy housing 48. The presence of ridge 54, when positioned with a complementary silicone layer structure, may help to maintain the position of the housing, and therefore of the ultrasonic radiating element, with respect to the ultrasonic catheter.

FIGS. 7A-C show an ultrasonic catheter with a modified connector 28 that can be used in combination with the arrangements and embodiments described above. The catheter 10 includes flexible tubular body. Distal to the connector 28 is the proximal port 24, which is in communication with the lumen of the tubular body 16. In the embodiment shown, the proximal port 24 is coaxial with the lumen of the tubular body 16. In use, blood from the treatment site may enter the lumen through the drainage holes 20 located on the distal region 12 of the catheter 10. Blood may then flow through the lumen and exit through proximal port 24 into a drainage kit. In some embodiments, a negative pressure is applied to the lumen of the catheter 10 to facilitate movement of the blood or other liquids at the treatment site proximally along the lumen and out the proximal port 24. In other embodiments, no external pressure is applied, and the blood or other liquid is permitted to flow from the treatment site to the proximal port 24, unaided by external pressure. In certain instances, the treatment site will possess relatively high pressure due to intracranial hemorrhaging. In such instances, the natural pressure of the treatment site may cause blood or other liquids to flow from the treatment site proximally along the lumen, and out the proximal port 24. Blood or other liquids may be drained at defined time intervals or continuously throughout the treatment. By continuously draining fluid the clot, under compression, may move towards the ultrasonic transducers for optimum ultrasound enhancement. Additionally, therapeutic agents may pass in the opposite direction. Such agents may enter the proximal port 24, pass distally through the lumen, and exit the catheter 10 through the drainage holes 20. In some embodiments, a positive pressure is applied to facilitate movement of the therapeutic agent or other liquid distally through the lumen and out the drainage holes 20. In other embodiments, no external pressure is applied, and the liquid is permitted to flow independently through the lumen. Therapeutic agents may be delivered in the form of a bolus within defined time intervals or continuously throughout the treatment. In order to allow for an exit path through the proximal port 24, the connector 28 is oriented at an angle with respect to the tubular body 16. In some embodiments, the connector lies at an angle between 10 and 90 degrees. In other embodiments, the connector 28 lies at an angle between 10 and 60 degrees, between 12 and 45 degrees, between 20 and 30 degrees, or approximately 22.5 degrees.

As described above with respect to other embodiments, the connector 28 may be configured to provide electrical connections to the ultrasound radiating elements. In the embodiments shown, however, the connector 28 may lie at an angle with respect to the tubular body 16. In certain embodiments, a wire may be soldered to a contact point on the inner portion of connector 28. An electrical contact may then be exposed on the outer surface of the connector 28 to provide for an electrical connection to an individual wire. By virtue of this design, each wire, and therefore each thermocouple or element, may be addressed independently. In alternative embodiments, two or more wires may be soldered to a single contact, thereby creating a single electrical connection. In other embodiments, the wires may meet electrical contacts at other points within the catheter 10. Alternatively, the wires may pass through the wall of the tubular body 16 and connect directly to external apparatuses.

The catheter 10 may be advanced until distal region 12 reaches the desired treatment site. For instance, the catheter 10 may be advanced through the cranial cavity until it is proximate to a blood clot. Therapeutic agents may then be delivered to the treatment site by the path described above. For instance, thrombolytic agents may be delivered to the treatment site, in order to dissolve the blood clot. In certain embodiments, ultrasonic energy may then be applied to the treatment site, as discussed above. Ultrasonic energy, alone or in combination with thrombolytic agents, may advantageously expedite dissolution of the blood clot. The ultrasonic energy may be applied continuously, periodically, sporadically, or otherwise. As the blood clot dissolves, excess blood may be drained from the treatment site through drainage holes 20. Excess blood entering the drainage holes 20 may pass through the lumen to the proximal port 24 and into a drainage kit or other disposal mechanism.

A modified embodiment of an ultrasonic catheter with a proximal port is shown in FIGS. 8A-B. In the embodiment shown, the proximal port 24 is located on the flexible tubular body 16 and is in communication with the lumen of the tubular body 16. In this configuration, the proximal port 24 is perpendicular to the axis of the tubular body 16, as opposed to the configuration depicted in FIGS. 7A-C, in which the proximal port 24 is coaxial with the tubular body 16. Positioning the proximal port 24 on the wall of the tubular body 16 removes the need for the connector to lie at an angle with respect to the tubular body 16.

As discussed above, therapeutic agents may flow through proximal port 24, distally through the lumen, and may exit the catheter 10 through the drainage holes 20 in distal region 12. Additionally, blood or other liquid may flow in the opposite direction, entering the catheter through drainage holes 20, flowing proximally through the lumen, and exiting the catheter 10 through proximal port 24 and into a drainage kit or other disposal means. Ultrasonic energy may also be applied periodically, continuously, sporadically, or otherwise throughout the process as desired. In certain embodiments, external pressure, negative or positive, may be applied in order to facilitate movement of liquids from the proximal port 24 through the lumen and out drainage holes 20, or in the opposite direction. In other embodiments, liquids are permitted to flow through the lumen, unaided by external pressure.

FIGS. 9A-F illustrate another arrangement for arranging the wires of an ultrasonic catheter. This arrangement can be used with the embodiments and arrangements described above. In this arrangement, a spiral groove extrusion 56 provides structural support to the tubular body 16. In certain embodiments, the groove extrusion 56 may be replaced by a similar structure formed by molding or any other method. The spiral groove design can provide improved kink resistance compared to a solid structure. The spiral groove extrusion 56 may be formed of a variety of different materials. For example, in one arrangement, metallic ribbons can be used because of their strength-to-weight ratios, fibrous materials (both synthetic and natural). In certain embodiments, stainless steel or tungsten alloys may be used to form the spiral groove extrusion 56. In certain embodiments, more malleable metals and alloys, e.g. gold, platinum, palladium, rhodium, etc. may be used. A platinum alloy with a small percentage of tungsten may be preferred due to its radiopacity. A sleeve 58 is arranged to slide over the spiral groove extrusion 56. The material for sleeve 58 may be formed of almost any biocompatible material, such as polyvinyl acetate or any biocompatible plastic or metal alloy. Distal extrusion 60 can house ultrasonic elements as well as drainage holes 20. The distal extrusion 60 can be formed of materials such as those described above with respect to spiral groove extrusion 56. Wires 38 are affixed to the distal extrusion 60 and connected to thermocouple or ultrasound radiating elements. A distal tip 62 is fitted to the end of distal extrusion 60.

FIG. 9C shows a cross-sectional view of the ultrasonic catheter shown in FIG. 9B. Outer diameter 64 may be approximately 0.2 inches. In other embodiments, the outer diameter 64 may be approximately 0.213 inches. The inner diameter 66 may be approximately 0.1 inches. In other embodiments, the inner diameter may be approximately 0.106 inches. As will be apparent, the dimensions of the inner and outer diameters will be selected according to the application intended based on, e.g., the diameter of the access path through the skull, the treatment site, the volume of therapeutic agent delivered, and anticipated volume of blood to be drained.

In the embodiment shown, the distal extrusion 60 may contain a window 68 in which an ultrasound radiating element may be affixed. In other embodiments, multiple ultrasonic radiating elements, each with a corresponding window 68, may be employed. As discussed above, the number, orientation, and relation of the ultrasonic radiating elements 36 may vary widely.

FIG. 9E shows a cross-sectional view of distal extrusion 60 shown in FIG. 9D. The drainage holes 20 are, in the embodiment shown, longitudinal gaps in the external surface of the distal extrusion 60. As can be seen in FIG. 9E, the distal extrusion 60 contains four drainage holes 20, each positioned approximately 90 degrees apart circumferentially. In other embodiments, two or three longitudinal drainage holes may be employed. In exemplary embodiments, five or more longitudinal drainage holes may be used.

FIGS. 10A-D show another embodiment of an ultrasonic catheter. As with FIGS. 9A-F, a spiral groove extrusion 56 provides the structural support to the flexible tubular body 16. Sleeve 58 is dimensioned to fit over the spiral extrusion 56. In the embodiment shown, the distal extrusion 60 has been excluded. Instead, the spiral extrusion 56 includes at its distal end drainage holes 20. Additionally, sleeve 58 also contains holes 70 designed to align with the drainage holes 20 of the spiral groove extrusion 56. In some embodiments, the spiral extrusion 56 and sleeve 58 may be joined before drainage holes 20 are drilled through both layers. Wires 38 are connected to ultrasound radiating elements 36. In the embodiment shown, the ultrasound radiating elements 36 and wires 38 are arranged to lie between the spiral extrusion 56 and the sleeve 58. As discussed above, the wires may be arranged in various other configurations. In certain embodiments, the wires may be arranged to lie within the spiral groove.

FIG. 10C shows a cross-sectional view of the proximal region of the ultrasonic catheter shown in FIG. 10B. The outer diameter 64 of the flexible tubular body 16 may be approximately 0.2 inches. In certain embodiments, the outer diameter 64 may be approximately 0.197 inches. The inner diameter 66 of the flexible tubular body 16 may be approximately 0.01 inches. In certain embodiments, the inner diameter 66 may be approximately 0.098 inches. As described above, the dimensions of the inner and outer diameters may vary based on the intended application.

As can be seen in FIG. 10D, in certain embodiments the spiral groove may become straight at the distal region 12 of the catheter. In this arrangement, the straightened region permits drainage holes 20 to be drilled in an arrangement of rows. Additionally, ultrasonic radiating elements 36 and wires 38 may be arranged to lie within the straight portion of the groove.

FIG. 11A-I show an ultrasonic catheter assembly according to one embodiment, in which a coaxial ultrasonic core is introduced into a separate external drain.

FIGS. 11A-C illustrate one embodiment of a drain 96. The distal portion 98 of the drain 96 includes drainage holes 100. In a preferred embodiment, the drainage holes 100 may span approximately 3 cm along the distal portion 98. In other embodiments, the drainage holes 100 may span shorter or longer distances, as desired. The drain 96 comprises an elongate tubular body 102, and may include distance markers 104. Distance markers 104 may be, for instance, colored stripes that surround the drain. In other embodiments, the distance markers 104 may be notches, grooves, radiopaque material, or any other material or structure that allows the regions to be visualized. The distance markers 104 may be spaced apart at regular intervals, for instance, every 2 cm, 5 cm, or other distance. In other embodiments they may be spaced in gradually increasing intervals, gradually decreasing intervals, irregularly, or in any other manner. In some embodiments, the distance between each marker will be written onto external surface of the drain. The presence of distance markers 104 may advantageously facilitate careful placement of the drain at a treatment site. In modified embodiments, a suture wing may be positioned at about 6 inches along the length of the catheter. Allowing a physician to visually observe the distance that the drain is advanced may improve control and placement precision.

The drain 96 includes a central lumen 106 which allows for the free flow of liquids from the drainage holes 100 towards the proximal portion 108 of the drain. As will be discussed in more detail below, in certain embodiments, any number of therapeutic compounds may be passed through the lumen 106 and out the drainage holes 100, where they then enter a treatment site. The diameter of the lumen may be approximately 2.2 mm, with an approximate outer diameter of 4.4 mm. In other embodiments, these diameters may be larger or smaller, as desired. As will be apparent to one of skill in the art, the inner and outer diameters of the drain 96 will be chosen based on desired treatment site, fluid flow rate through the lumen, the material used to construct the drain, and the size of the ultrasonic core or any other element intended to pass therethrough. In one arrangement, the drain may operate at a flow rate of approximately 20 ml per hour, at a pressure of 10 mmHg.

FIGS. 11D-E show one embodiment of an ultrasonic core 110. The ultrasonic core 110 comprises an elongate shaft 112 and hub 114. Ultrasonic elements 36 are positioned coaxially with the elongate shaft 112. In certain embodiments, the ultrasonic core includes between one and four ultrasonic elements 36. In other embodiments, five or more ultrasonic elements 36 may be included. The elongate shaft 112 is dimensioned so as to be removably received within drain 96.

Accordingly, in certain embodiments, the outer diameter of the elongate shaft is approximately 0.8 mm, and the length of the elongate shaft is approximately 31 cm.

The hub 114 is attached to elongate shaft 112 through a tapered collar 116. A proximal fluid port 118 is in fluid communication with the hub. Fluids, such as therapeutic drugs, may be injected down the core through proximal fluid port 118 towards the treatment zone. Introducing fluids in this manner may permit the use of a smaller bolus of therapeutic drug as compared to introducing fluids through the drain as discussed above. Alternatively, fluids may be injected into the lumen 106 of drain 96 through use of a Tuohy-Borst adapter attached thereto. Injecting fluids through the lumen 106 of the drain 96 may require lower injection pressure, although a larger bolus of therapeutic drug may be necessary. In either configuration, the therapeutic drug ultimately flows out of drainage holes 100 located in the distal region 98 of drain 96.

FIGS. 11F-I illustrate the catheter assembly 120 in which ultrasonic core 110 is inserted within lumen 106 of drain 96. In certain embodiments, the drain 96 may be advanced to the treatment site, followed by insertion of the ultrasonic core 110 within the drain. For instance, the drain may be tunneled under the scalp, through a bore in the skull, and into the brain. Then the ultrasonic core 110 may be inserted into the drain 96, and advanced until the elongate shaft 112 reaches the distal region 98 of drain 96.

Upon insertion, ultrasonic elements 36 may be positioned near the drainage holes 100, allowing for the application of ultrasonic energy to the treatment site. As can be seen in FIGS. 11H and 11I, the distal end of the elongate shaft 112 of ultrasonic core 110 may include one or more ultrasonic elements 36. When advanced into the distal region 98 of drain 96, the ultrasonic radiating element 36 would be located within the region containing drainage holes 100. As discussed in more detail above, application of ultrasonic energy to a treatment site may aid in dissolution of a blood clot. Introduction of therapeutic drugs through the catheter assembly 120 and out drainage holes 110 may further aid in this process. As the clot is dissolved, excess blood or other fluid may be received within the drainage holes 100 and evacuated from the treatment site.

Figure 12A:
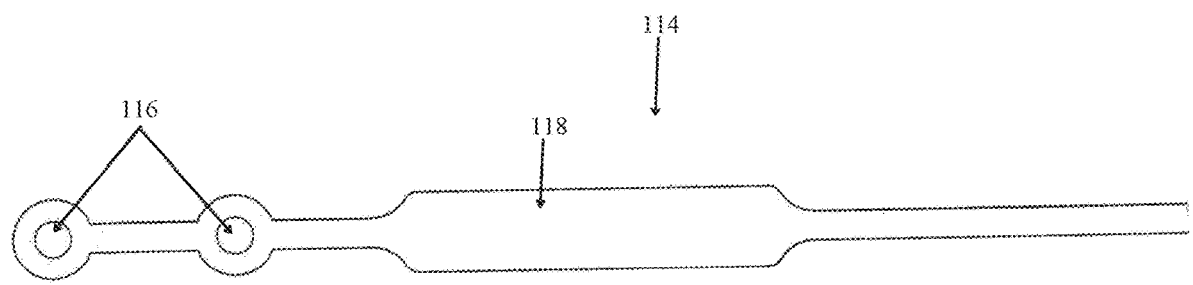
FIG. 12A is a schematic view of an ultrasonic core wire, according to one embodiment.
Figure 12B:
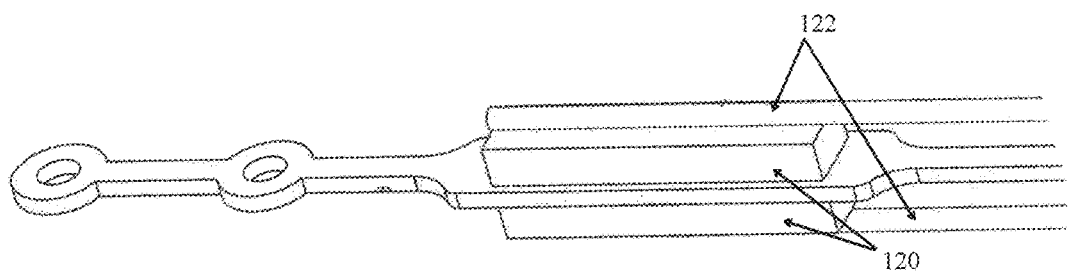
FIG. 12B is a perspective view of an ultrasonic core wire with ultrasonic transducers affixed thereto.

With reference now to FIGS. 12A and 12B, in alternative embodiments two separate lumens may be included, one for fluid evacuation and one for fluid delivery. FIG. 12A shows a catheter In certain embodiments, continuous fluid flow may be possible. For example, application of positive pressure at the drug delivery port and simultaneous application of vacuum at the drainage port may provide for continuous removal of toxic blood components. Alternatively, influx and efflux could be accomplished separately and intermittently to allow drugs to have a working dwell time. In certain embodiments, the catheter design could spatially separate drainage holes from drug delivery holes and inlet ports, with the ultrasound transducers in between. The ultrasound radiating radially may prevent influx from going directly to efflux.

Figure 12C:
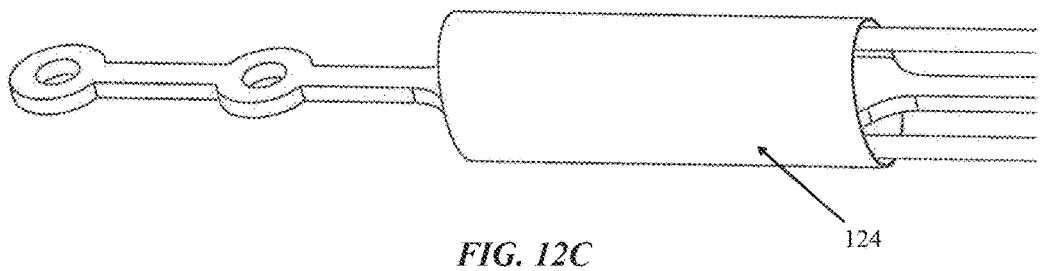
FIG. 12C is a perspective view of an ultrasonic core wire with a polyimide shell surrounding ultrasonic transducers.

FIG. 12A-C illustrate one embodiment of an ultrasonic element and core wire. The ultrasonic core wire 114 comprises locking apertures 116 and pad 118. When integrated within a completed ultrasonic core or ultrasonic catheter, the ultrasonic core wire 114 may be embedded in silicone. The two locking apertures 116 allow for silicone to flow through the opening, thereby providing for a mechanical lock that secures the element into the silicone. The locking apertures need not be circular, but may be any shape that permits silicone to flow therethrough to create a mechanical lock.

Additionally, in certain embodiments there may be one locking aperture 116. In other embodiments, there may be two, three, four, or more locking apertures 116, as desired. Ultrasonic transducers 120 are affixed to either side of pad 118. RF wires 122 are then mounted to be in communication with ultrasonic transducers 120. A polyimide shell 124 may be formed around the assembly of the pad 118, ultrasonic transducers 120, and RF wires 122, as shown in FIG. 12C. The polyimide shell may be oval-shape to aid in correct orientation of the ultrasonic element, and to minimize the use of epoxy in manufacturing.

Figure 13:
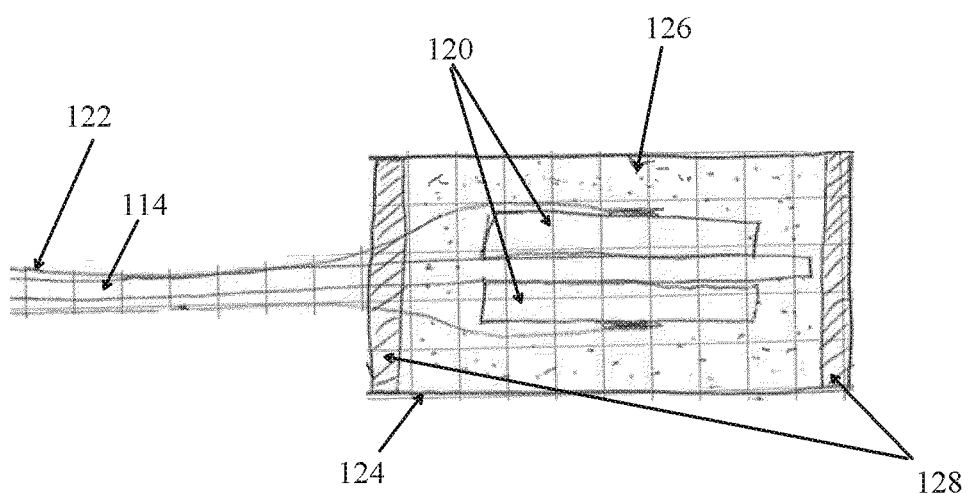
FIG. 13 is a schematic illustration of an ultrasonic element within a fluid-filled chamber, according to one embodiment.

FIG. 13 illustrates an ultrasonic element suspended in a fluid-filled chamber. The fluid-filled chamber 126 is bounded circumferentially by a polyimide shell 124, with plugs 128 defining the ends of the fluid-filled chamber. Ultrasonic core wire 114 and RF wires 122 penetrate one of the plugs 128 to enter the fluid-filled chamber 126. A fluid-tight seal is provided at the point of penetration to ensure that the chamber retains its fluid. Within the fluid-filled chamber 126 are the ultrasonic transducers 120 affixed to the ultrasonic core wire 114 and in communication with RF wires 122. This design may provide for several advantages over other configurations. For instance, potting ultrasonic elements in epoxy may lead to absorption of water by the epoxy, potentially causing delamination of an ultrasonic element from the potting material. Delamination of an element reduces the ability of the ultrasonic energy to be transferred from the ultrasonic element to the surrounding tissue. Suspending an ultrasonic element within a fluid-filled chamber may advantageously avoid this problem. The ultrasonic energy emitted by the ultrasonic elements transfers easily in fluid, and there is no risk of delamination. In addition, suspending ultrasonic elements within a fluid-filled chamber may advantageously reduce the number of components needed for an ultrasonic core, as well as potentially reducing assembly time.

Figure 14:
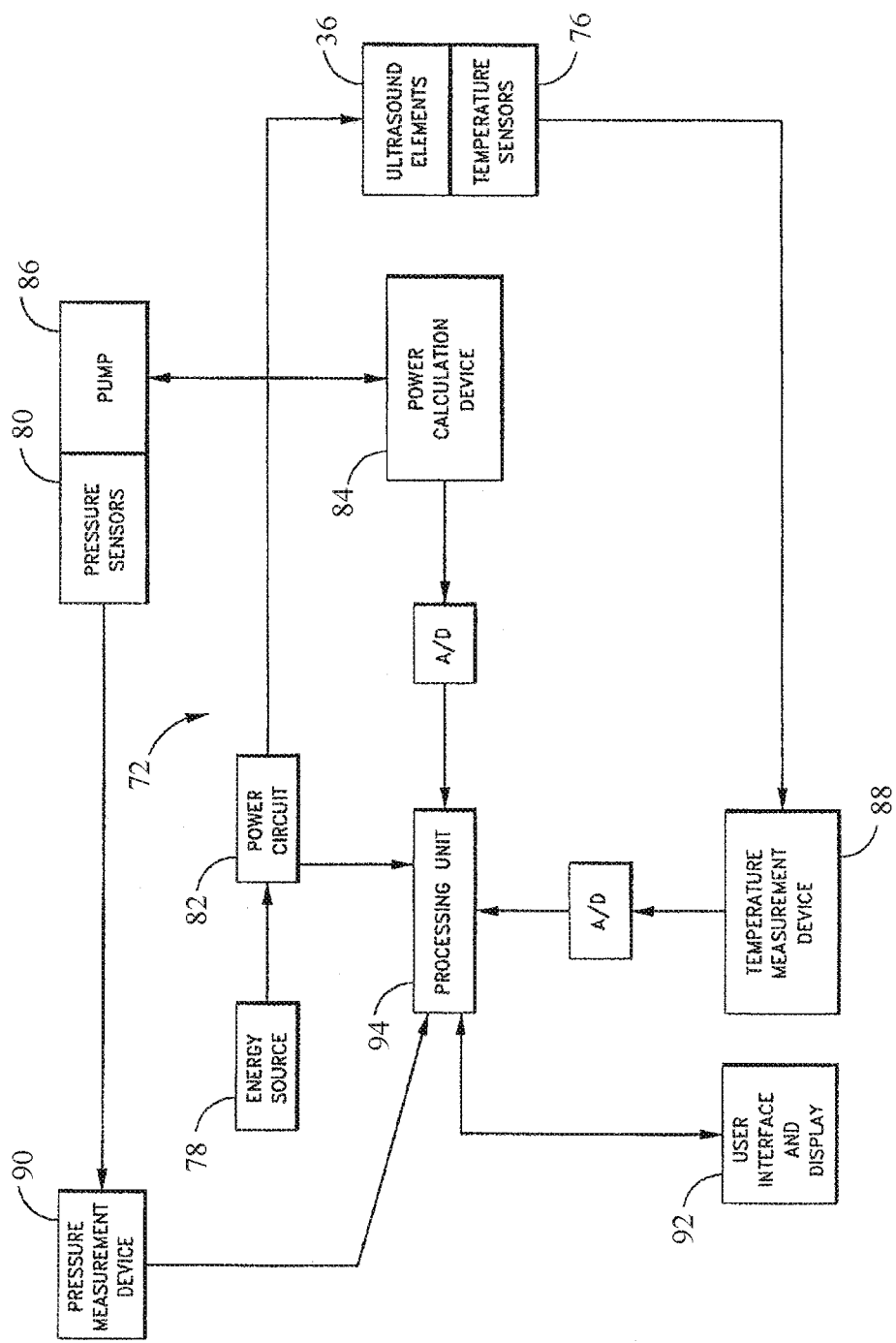
FIG. 14 is a block diagram of a feedback control system for use with an ultrasonic catheter.

FIG. 14 schematically illustrates one embodiment of a feedback control system 72 that can be used with the catheter 10. The feedback control system 72 allows the temperature at each temperature sensor 76 to be monitored and allows the output power of the energy source 78 to be adjusted accordingly. In some embodiments, each ultrasound radiating element 36 is associated with a temperature sensor 76 that monitors the temperature of the ultrasound radiating element 36 and allows the feedback control system 72 to control the power delivered to each ultrasound radiating element 36. In some embodiments, the ultrasound radiating element 36 itself is also a temperature sensor 76 and can provide temperature feedback to the feedback control system 72. In addition, the feedback control system 72 allows the pressure at each pressure sensor 80 to be monitored and allows the output power of the energy source 78 to be adjusted accordingly. A physician can, if desired, override the closed or open loop system.

In an exemplary embodiment, the feedback control system 72 includes an energy source 78, power circuits 82 and a power calculation device 84 that is coupled to the ultrasound radiating elements 36 and a pump 86. A temperature measurement device 88 is coupled to the temperature sensors 76 in the tubular body 16. A pressure measurement device 90 is coupled to the pressure sensors 80. A processing unit 94 is coupled to the power calculation device 84, the power circuits 82 and a user interface and display 92.

In an exemplary method of operation, the temperature at each temperature sensor 76 is determined by the temperature measurement device 88. The processing unit 94 receives each determined temperature from the temperature measurement device 88. The determined temperature can then be displayed to the user at the user interface and display 92.

In an exemplary embodiment, the processing unit 94 includes logic for generating a temperature control signal. The temperature control signal is proportional to the difference between the measured temperature and a desired temperature. The desired temperature can be determined by the user (as set at the user interface and display 92) or can be preset within the processing unit 94.

In such embodiments, the temperature control signal is received by the power circuits 82. The power circuits 82 are configured to adjust the power level, voltage, phase and/or current of the electrical energy supplied to the ultrasound radiating elements 36 from the energy source 78. For example, when the temperature control signal is above a particular level, the power supplied to a particular group of ultrasound radiating elements 36 is reduced in response to that temperature control signal. Similarly, when the temperature control signal is below a particular level, the power supplied to a particular group of ultrasound radiating elements 36 is increased in response to that temperature control signal. After each power adjustment, the processing unit 94 monitors the temperature sensors 76 and produces another temperature control signal which is received by the power circuits 82.

In an exemplary method of operation, the pressure at each pressure sensor 80 is determined by the pressure measurement device 90. The processing unit 94 receives each determined pressure from the pressure measurement device 90. The determined pressure can then be displayed to the user at the user interface and display 92.

In an exemplary embodiment, the processing unit 94 includes logic for generating a pressure control signal. The pressure control signal is proportional to the difference between the measured pressure and a desired pressure. The desired pressure can be determined by the user (as set at the user interface and display 92) or can be preset within the processing unit 94.

As noted above, it is generally desirable to provide low negative pressure to the lumen in order to reduce the risk of sucking solid material, such as brain matter, into the lumen. Furthermore, because reduction of intracranial pressure is often desirable in treating ICH, it is often desirable to deliver fluids with little pressure differential between the delivery pressure and the intracranial pressure around the catheter. Accordingly, the processing unit 94 can be configured to monitor the pressure and modify or cease the delivery of fluid and/or increase evacuation of fluid to the treatment site if intracranial pressure increases beyond a specified limit.

In other embodiments, the pressure control signal is received by the power circuits 82. The power circuits 82 are configured to adjust the power level, voltage, phase and/or current of the electrical energy supplied to the pump 86 from the energy source 78. For example, when the pressure control signal is above a particular level, the power supplied to a particular pump 86 is reduced in response to that pressure control signal. Similarly, when the pressure control signal is below a particular level, the power supplied to a particular pump 86 is increased in response to that pressure control signal. After each power adjustment, the processing unit 94 monitors the pressure sensors 80 and produces another pressure control signal which is received by the power circuits 82.

In an exemplary embodiment, the processing unit 94 optionally includes safety control logic. The safety control logic detects when the temperature at a temperature sensor 76 and/or the pressure at a pressure sensor 80 exceeds a safety threshold. In this case, the processing unit 94 can be configured to provide a temperature control signal and/or pressure control signal which causes the power circuits 82 to stop the delivery of energy from the energy source 78 to that particular group of ultrasound radiating elements 36 and/or that particular pump 86.

Consequently, each group of ultrasound radiating elements 36 can be identically adjusted in certain embodiments. For example, in a modified embodiment, the power, voltage, phase, and/or current supplied to each group of ultrasound radiating elements 36 is adjusted in response to the temperature sensor 76 which indicates the highest temperature. Making voltage, phase and/or current adjustments in response to the temperature sensed by the temperature sensor 76 indicating the highest temperature can reduce overheating of the treatment site.

The processing unit 94 can also be configured to receive a power signal from the power calculation device 84. The power signal can be used to determine the power being received by each group of ultrasound radiating elements 36 and/or pump 86. The determined power can then be displayed to the user on the user interface and display 92.

As described above, the feedback control system 72 can be configured to maintain tissue adjacent to the energy delivery section 18 below a desired temperature. For example, in certain applications, tissue at the treatment site is to have a temperature increase of less than or equal to approximately 6 degrees C. As described above, the ultrasound radiating elements 36 can be electrically connected such that each group of ultrasound radiating elements 36 generates an independent output. In certain embodiments, the output from the power circuit maintains a selected energy for each group of ultrasound radiating elements 36 for a selected length of time.

The processing unit 94 can comprise a digital or analog controller, such as a computer with software. In embodiments wherein the processing unit 94 is a computer, the computer can include a central processing unit ("CPU") coupled through a system bus. In such embodiments, the user interface and display 92 can include a mouse, a keyboard, a disk drive, a display monitor, a nonvolatile memory system, and/or other computer components. In an exemplary embodiment, program memory and/or data memory is also coupled to the bus.

In another embodiment, in lieu of the series of power adjustments described above, a profile of the power to be delivered to each group of ultrasound radiating elements 36 can be incorporated into the processing unit 94, such that a preset amount of ultrasonic energy to be delivered is preprofiled. In such embodiments, the power delivered to each group of ultrasound radiating elements 36 is provided according to the preset profiles.

In an exemplary embodiment, the ultrasound radiating elements are operated in a pulsed mode. For example, in one embodiment, the time average power supplied to the ultrasound radiating elements is between about 0.1 watts and about 2 watts. In another embodiment, the time average power supplied to the ultrasound radiating elements is between about 0.5 watts and about 1.5 watts. In yet another embodiment, the time average power supplied to the ultrasound radiating elements is approximately 0.6 watts or approximately 1.2 watts. In an exemplary embodiment, the duty cycle is between about 1% and about 50%. In another embodiment, the duty cycle is between about 5% and about 25%. In yet another embodiment, the duty cycles is approximately 7.5% or approximately 15%. In an exemplary embodiment, the pulse averaged power is between about 0.1 watts and about 20 watts. In another embodiment, the pulse averaged power is between approximately 5 watts and approximately 20 watts. In yet another embodiment, the pulse averaged power is approximately 8 watts or approximately 16 watts. The amplitude during each pulse can be constant or varied.

In an exemplary embodiment, the pulse repetition rate is between about 5 Hz and about 150 Hz. In another embodiment, the pulse repetition rate is between about 10 Hz and about 50 Hz. In yet another embodiment, the pulse repetition rate is approximately 30 Hz. In an exemplary embodiment, the pulse duration is between about 1 millisecond and about 50 milliseconds. In another embodiment, the pulse duration is between about 1 millisecond and about 25 milliseconds. In yet another embodiment, the pulse duration is approximately 2.5 milliseconds or approximately 5 milliseconds.

For example, in one particular embodiment, the ultrasound radiating elements are operated at an average power of approximately 0.6 watts, a duty cycle of approximately 7.5%, a pulse repetition rate of approximately 30 Hz, a pulse average electrical power of approximately 8 watts and a pulse duration of approximately 2.5 milliseconds.

In an exemplary embodiment, the ultrasound radiating element used with the electrical parameters described herein has an acoustic efficiency greater than approximately 50%. In another embodiment, the ultrasound radiating element used with the electrical parameters described herein has an acoustic efficiency greater than approximately 75%. As described herein, the ultrasound radiating elements can be formed in a variety of shapes, such as, cylindrical (solid or hollow), flat, bar, triangular, and the like. In an exemplary embodiment, the length of the ultrasound radiating element is between about 0.1 cm and about 0.5 cm, and the thickness or diameter of the ultrasound radiating element is between about 0.02 cm and about 0.2 cm.

With reference now to FIG. 15, in one embodiment of a treatment protocol, patients can be taken to an operating room and placed under general anesthesia for ultrasound and drainage catheter insertion. Patients can be registered using electromagnetic (EM) stealth, based on CT parameters for stereotactic placement of catheters using the Medtronic EM Stealth navigation system. However, as described above, in modified embodiments, other navigation techniques and tools could be used. Using such navigation systems, an entry point for the burr hole and target point in the hemorrhage for the catheter tips can be chosen. In some embodiments, the burr-hole can be located for an occipital approach if the patient has an intraventricular hemorrhage. In some embodiments, the burr-hole can be located for a more frontal approach if the patient has an intracerebral hemorrhage located in the frontal portion of the brain. It should be appreciated that the location of the burr-hole or drill hole can be selected to reduce the path length between the blood clot and the hole in the patient's skull. In addition, it may be desirable in some cases to approach the blood clot from an angle that avoids certain portions of the brain.

In the illustrated embodiment, a Stealth guidance system (or other guidance system or technique) can used to place a 12 French peel-away introducer through the burr hole into the desired location in the hemorrhage, to accommodate placement of the ultrasonic catheter 10. In modified arrangements, a different size and/or type of introducer could be used and/or the ultrasonic catheter can be inserted without an introducer.

As shown in FIG. 15, the catheter 10 can be with the peel away introducer and the position confirmed by neuro-navigation or other navigation technique. In one embodiment, the two catheters can then be tunneled out through a separate stab wound in the skin and secured to the patient. A portable CT scan can be done at the completion of the procedure to confirm acceptable catheter placement. In one embodiment, the distal tip of the ultrasonic catheter 10 is generally positioned long the longitudinal center (measured along the axis of the catheter) of the hemorrhage. As described above, in other embodiments, an ultrasonic core can be place through a lumen in the catheter (see e.g., FIGS. 1A-F). In other embodiments, the ultrasonic catheter can be placed along side the catheter.

In one embodiment of use, patients with ICH or IVH can be treated after the CT scans to confirm no active bleeding and expansion of the hematoma. In one embodiment, such scans can be obtained approximately 3 hours after catheter placement but before treatment had begun with ultrasound and thrombolytic. In some embodiments, the treatment may include injecting a thrombolytic drug into the hemorrhage through the catheter. The catheter is then flushed and clamped for about 1 hour with the drainage close and then opened to closed drainage at 10 cm below the lesion thus allowing the full dose of the thrombolytic drug to be delivered into the clot. In one embodiment of use, patients with intraventricular hemorrhages, 1 mg of rt-PA can be injected and 0.3 mg rt-PA can be injected in patients with intraparenchymal hemorrhages.

In one embodiment of use, following about 1 hour of drug treatment, the closed drainage can be opened below the lesion. The injections can be repeated about every 8 hours (e.g., at about 8 hours and about 16 hours from the time of the initial injection) for a total of 3 doses over a period of about 24 hours. Computer Tomography (CT) imaging can be performed at appropriate time during the treatment to determined rate of lysis and to monitor the progress of clot lysis. The drainage may also be evaluated by performing a CT. The ultrasound remains operating all the time during the treatment, and may be turned off only during the CT imaging for the least possible length of time. Thus, in some embodiments, the ultrasound may be turned on at the time of the initial injection and delivered continuously at the catheter tip for up to about 24 hours.

Ultrasound energy can be delivered for a duration sufficient to enable adequate drug distribution in and/or around the blood clot. This can be accomplished by either intermittent or continuous delivery of ultrasound energy. For example, ultrasound energy can be delivered for a set time period to adequately distribute the drug to the blood clot, and then turned off to allow the drug to act on the blood clot. Alternatively, ultrasound energy can be delivered substantially continuously after the drug has been delivered to the blood clot to continuously redistribute the drug into the blood clot as the blood clot is successfully lysed. In addition, ultrasound energy can be delivered intermittently to reduce heating. Also, as described in U.S. application Ser. No. 11/971,172, filed Jan. 8, 2008, which is hereby incorporated by reference herein in its entirety, the power parameters controlling the delivery of ultrasound energy can be randomized or varied according to complex non-linear algorithms in order to enhance the efficacy of the ultrasound treatment.

Drug delivery can be controlled by monitoring, for example, lysis byproducts such as D-dimer in the effluent evacuated from the blood clot. A high and/or increasing concentration of D-dimer in the effluent can indicate that lysis of the blood clot is proceeding adequately, and therefore drug delivery can be maintained, reduced or stopped. A low or decreasing concentration of D-dimer in the effluent can indicate that lysis of the blood clot is inadequate or slowing or that the clot is nearly dissolved, and therefore drug delivery can be increased if the clot is not nearly dissolved, and reduced or stopped if lysis is almost complete. Alternatively, lytic concentration can be monitored to determine whether more drug should be delivered and whether lysis is complete. In some embodiments, as lysis of the blood clot proceeds, lytic is freed from the lysed clot, thereby increasing the concentration of lytic in the effluent. Therefore, increased lytic concentration can correlate to lysis completion. One way of determining the concentration of lytic and/or D-dimer in the effluent is to measure the color of the effluent that is evacuated from the blood clot. The redder the effluent, the greater the concentration of lytic and/or D-dimer in the effluent.

In some embodiments, neuroprotective drugs or agents that assist in the functional recovery and/or the reduction of cell and tissue damage in the brain can also be delivered to the brain and blood clot with the methods and apparatus described above. These neuroprotective drugs or agents can be delivered before, with, or after the delivery of the thrombolytic drugs. Delivery of these drugs using the methods and apparatus described above is particularly useful where the drug delivery through the blood brain barrier is enhanced with ultrasound treatment, or where ultrasound enhances cell penetration by the drug, or where the drug is sonodynamic.

Another embodiment of an ultrasonic catheter is shown in FIGS. 16A-E. Similar to the embodiments described above with respect to FIGS. 2A-D, the catheter includes wires 38 embedded within the wall of the tubular body 16. The wires 38 are connected to and may control ultrasonic radiating elements 36 located within the distal region 12 of the catheter 10. The wires extend from the proximal end of the tubular body 16. In certain embodiments, the wires extend more than six inches from the proximal end, so as to facilitate electrical connection with external devices. Drainage holes 20 are positioned in the distal region 12 of the catheter 10, near the ultrasonic radiating elements 36. In other embodiments, thermocouples, pressure sensors, or other elements may also be disposed within the distal region 12. The distal region 12 may be composed of silicone or other suitable material, designed with drainage holes 20 as discussed above. Ultrasonic radiating elements 36 may be embedded within the wall of the distal region 12, surrounded by the silicone or other material. In various embodiments, there may be as few as one and as many as 10 ultrasonic radiating elements 36 can be embedded with the distal region 12 of the device. The elements 36 can be equally spaced in the treatment zone. In other embodiments, the elements 36 can be grouped such that the spacing is not uniform between them. In an exemplary embodiment illustrated in FIGS. 16B-D, the catheter 10 includes four ultrasonic radiating elements 36. In this four-element configuration, the elements can be spaced apart as pairs, with each pair located at a similar longitudinal position, but separated by 180 degrees circumferentially. The pairs of offset from one another both by 90 degrees circumferentially and by a longitudinal distance along the length of the catheter 10. As will be apparent to the skilled artisan, various other combinations of ultrasonic radiating elements are possible.

While the foregoing detailed description has set forth several exemplary embodiments of the apparatus and methods of the present invention, it should be understood that the above description is illustrative only and is not limiting of the disclosed invention. It will be appreciated that the specific dimensions and configurations disclosed can differ from those described above, and that the methods described can be used within any biological conduit within the body.

What is claimed is:

1. An ultrasound catheter for treatment of a blood clot resulting from an intracranial hemorrhage comprising:
    an elongate tubular body having a distal portion and a proximal portion, the elongate tubular body comprising an inner surface defining a lumen and an outer surface;
    a plurality of ultrasound radiating elements positioned in the distal portion of the elongate tubular body between the inner and outer surfaces of the tubular body;
    a surface configured to form an electrical connection on the proximal portion of the tubular body comprising annular rings in electrical connection with the plurality of radiating elements and a proximal port located on the proximal portion of the tubular body, the proximal port adjacent and distal to the electrical connection,
        wherein the lumen includes a plurality of ports on the distal portion of the elongate tubular body configured to allow fluid to flow therethrough, wherein the proximal port opens on an outer surface of the elongate tubular body and is perpendicular to a longitudinal axis of the elongate tubular body; and
    a stylet configured to be received within the lumen.

2. The catheter of claim 1, wherein wires connect the electrical connection to the ultrasound radiating elements in the elongate tubular body, wherein the wires are embedded within the elongate tubular body.

3. The catheter of claim 1, further comprising a proximal port co-linear with the lumen.

4. The catheter of claim 1, wherein the ultrasound radiating elements are potted in epoxy.

5. The catheter of claim 1, wherein the ultrasound radiating elements are suspended in a fluid.

6. The catheter of claim 1, wherein the ultrasound radiating elements are positioned within a window on the outer surface of the elongate tubular body.

7. The catheter of claim 1, wherein the ultrasound radiating elements are positioned in the distal portion of the elongate tubular body.

8. The catheter of claim 1, wherein the elongate tubular body comprises a metal extrusion surrounded by a sleeve.

9. The catheter of claim 8, wherein elongate tubular body further comprises a distal extrusion configured to be affixed to the metal extrusion, wherein the distal extrusion houses the ultrasound radiating elements.

10. The catheter of claim 8, wherein, the metal extrusion includes the distal portion containing the plurality of ports.

11. The catheter of claim 8, wherein the extrusion is a spiral extrusion.

12. The catheter of claim 1, wherein the ports are circular.

13. The catheter of claim 1, wherein the ports comprise longitudinal openings in the distal portion of the elongate tubular body.

14. The catheter of claim 1, further comprising distance markers on the elongate tubular body.

15. An ultrasound catheter comprising:
    an elongate tubular body having a distal portion and a proximal portion, the elongate tubular body comprising walls defining a first drainage lumen within the elongate tubular body and a delivery lumen within the elongate tubular body;
    wherein the elongate tubular body does not have sufficient hoop strength, kink resistance, rigidity, and structural support to be pushed through an opening in a skull and into brain tissue;

wherein the drainage lumen includes a plurality of drainage ports on the distal portion of the elongate tubular body configured to allow fluid to flow therethrough;

wherein the delivery lumen includes a plurality of delivery ports on the distal portion of the elongate tubular body configured to allow fluid to flow therethrough;

a plurality of ultrasound radiating elements positioned within, the walls of the elongate tubular body, wherein the ultrasound radiating elements are piezoelectric ceramic oscillators;

a surface configured to form an electrical connection on the proximal portion of the elongate tubular body and a proximal port located adjacent and distal to the electrical connection, wherein the proximal port opens on an outer surface of the elongate tubular body in the proximal portion, wherein the proximal port is perpendicular to a longitudinal axis of the elongate tubular body; and a stylet configured to be received within the drainage lumen.

16. The ultrasound catheter of claim 15, wherein the elongate tubular body is formed in part from silicone.

17. The ultrasound catheter of claim 15, wherein the elongate tubular body has material properties same as that of standard external ventricular drainage (EVD) catheter.

18. The catheter of claim 1, wherein the elongate tubular body has material properties the same as that of standard external ventricular drainage (EVD) catheter, wherein the elongate tubular body does not have sufficient hoop strength, kink resistance, rigidity, and structural support to be pushed through an opening in a skull and into brain tissue.

19. The catheter of claim 1, wherein the electrical connection is located at an angle with respect to the elongate tubular body.

20. The catheter of claim 19, wherein the angle ranges between 10 and 60 degrees.

21. The catheter of claim 19, wherein the angle ranges between 12 and 45 degrees.

22. The catheter of claim 19, wherein the angle is 22.5 degrees.

* * * * *